United States Patent [19]

Maier et al.

[11] Patent Number: 5,466,687
[45] Date of Patent: Nov. 14, 1995

[54] ARYLIDENE-1-AZACYCLOALKANES AND ARYLALKYL-1-AZACYCLO-ALKANES, THEIR SALTS, MEDICAMENTS CONTAINING THESE COMPOUNDS AND THEIR USE, AND PROCESSES FOR THEIR PREPARATION

[75] Inventors: Roland Maier, Biberach; Peter Müller, Mittelbiberach; Eberhard Woitun, Biberach; Rudolf Hurnaus, Biberach; Michael Mark, Biberach; Bernhard Eisele, Biberach; Ralph-Michael Budzinski, Biberach; Gerhard Hallermayer, Maselheim-Sulmingen, both of Germany

[73] Assignee: Dr. Karl Thomae GmbH, Biberach an der Riss, Germany

[21] Appl. No.: 218,092

[22] Filed: Mar. 25, 1994

Related U.S. Application Data

[63] Continuation-in-part of Ser. No. 139,255, Oct. 20, 1993, abandoned.

[30] Foreign Application Priority Data

Oct. 22, 1992 [DE] Germany ............................ 42 35 590.7
Feb. 10, 1993 [DE] Germany ............................ 43 03 840.9

[51] Int. Cl.$^6$ .......................... A61K 31/55; A61K 31/54; C07D 405/10; C07D 279/06
[52] U.S. Cl. .................. 514/212; 514/226.8; 514/228.8; 514/326; 514/372; 514/374; 514/385; 514/399; 540/598; 540/601; 540/603; 544/54; 544/96; 544/335; 546/209; 546/210; 548/146; 548/238; 548/314.7
[58] Field of Search ...................... 540/598, 601, 540/603; 544/54, 96, 335; 546/209, 210; 548/146, 238, 314.7; 514/212, 226.8, 228.8, 326, 372, 374, 385, 399

[56] References Cited

U.S. PATENT DOCUMENTS

| | | | |
|---|---|---|---|
| 4,863,932 | 9/1989 | Sinensky | 514/307 |
| 5,169,844 | 12/1992 | Commons et al. | 514/211 |
| 5,187,271 | 2/1993 | Bovy et al. | 548/314.7 |

FOREIGN PATENT DOCUMENTS

| | | |
|---|---|---|
| 0420116 | 4/1991 | European Pat. Off. . |
| 0468434 | 1/1992 | European Pat. Off. . |
| 0506072 | 1/1992 | European Pat. Off. . |

OTHER PUBLICATIONS

H. Buchwald, "Cholesterol inhibition, cancer, and chemotheraphy", vol. 339, May 9, 1992, 1154–1156.
The Merck Index, Eleventh Edition, 1989, 878–879, 1351–1352.

Primary Examiner—Mukund J. Shah
Assistant Examiner—Matthew V. Grumbling
Attorney, Agent, or Firm—Robert P. Raymond; Alan R. Stempel; Mary-Ellen M. Devlin

[57] ABSTRACT

The invention relates to arylidene-1-azacycloalkanes and arylalkyl-1-azacycloalkanes of the general formula

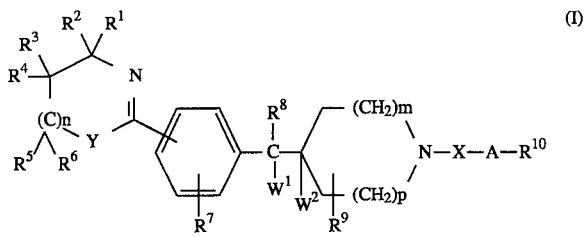

(wherein n, m, p, A, $W^1$, $W^2$, X, Y, and $R^1$ to $R^{11}$ are as defined in claim 1) and the isomers, isomer mixtures and salts thereof, which have useful properties, in particular an inhibitory effect on cholesterol biosynthesis.

17 Claims, No Drawings

ARYLIDENE-1-AZACYCLOALKANES AND ARYLALKYL-1-AZACYCLO-ALKANES, THEIR SALTS, MEDICAMENTS CONTAINING THESE COMPOUNDS AND THEIR USE, AND PROCESSES FOR THEIR PREPARATION

RELATED APPLICATIONS

This application is a continuation-in-part of application Ser. No. 139,255, filed on Oct. 20, 1993, now abandoned.

FIELD OF THE INVENTION

The present invention relates to arylidene-1-azacycloalkanes and arylalkyl-1-azacycloalkanes, their salts with physiologically tolerable organic and inorganic acids, processes for the preparation of these compounds and medicaments containing them.

BACKGROUND AND BRIEF DESCRIPTION OF THE INVENTION

The compounds according to the invention are inhibitors of cholesterol biosynthesis, in particular inhibitors of the enzyme 2,3-epoxysqualene-lanosterol cyclase, a key enzyme of cholesterol biosynthesis. The compounds according to the invention are suitable for the treatment and prophylaxis of hyperlipidaemias, hypercholesterolaemias and of atherosclerosis. Further possible applications include the treatment of hyperproliferative skin and vascular disorders, tumours, gallstone trouble and mycoses.

Compounds which intervene in cholesterol biosynthesis are important for the treatment of a number of syndromes. Particular mention may be made in this regard of hypercholesterolaemias and hyperlipidaemias, which are risk factors for the formation of atherosclerotic vascular changes and their sequelae such as, for example, coronary heart disease, cerebral ischaemia, intermittent claudication and gangrene.

The importance of excessive serum cholesterol levels as a main risk factor for the formation of atherosclerotic vascular changes is generally recognized. Extensive clinical studies have led to the realization that the risk of suffering from coronary heart diseases can be decreased by reduction of the serum cholesterol (Current Opinion in Lipidology 2(4), 234 [1991]). Since the largest part of the cholesterol in the body is self-synthesized and only a small part is absorbed from food, the inhibition of biosynthesis represents a particularly attractive route to lower increased cholesterol levels.

In addition, treatment of hyperproliferative skin and vascular disorders and of oncoses, the treatment and prophylaxis of gallstone trouble and use in mycoses are described as further possible applications for cholesterol biosynthesis inhibitors. In this connection, in the latter case, intervention in ergosterol biosynthesis in fungal organisms, proceeds to a large extent in a manner analogous to the intervention in cholesterol biosynthesis in mammalian cells.

Cholesterol or ergosterol biosynthesis proceeds, starting from acetic acid, via a relatively large number of reaction steps. This multistage process offers a number of possibilities for intervention, of which the following may be mentioned as examples:

β-Lactones and β-lactams having potential anti-hypercholesterolaemic action which inhibit the enzyme 3-hydroxy-3-methylglutaryl-coenzyme A (HMG-CoA) synthase have been described (see J. Antibiotics 40, 1356 [1987], U.S. Pat. No. 4,751,237, EP-A-0462667 and U.S. Pat. No. 4,983,597).

Inhibitors of the enzyme HMG-CoA reductase are 3,5-dihydroxycarboxylic acids of the mevinolin type and their δ-lactones, whose representatives lovastatin, simvastatin and pravastatin are used in the therapy of hypercholesterolaemias. Further possible applications of these compounds are in the treatment of fungal infections (U.S. Pat. No. 4,375,475, EP-A-0113881, U.S. Pat. No. 5,106,992), skin disorders (EP-A-0369263) and gallstone trouble and oncoses (U.S. Pat. No. 5,106,992; Lancet 339, 1154–1156 [1992]). The inhibition of smooth muscle cell proliferation by lovastatin is described in Cardiovasc. Drugs Ther. 5, Suppl. 3, 354 [1991].

The suitability of inhibitors of the enzyme squalene synthetase e.g. isoprenoid -(phosphinylmethyl)phosphonates, for the treatment of hypercholesterolaemias, gallstone trouble and oncoses is described in EP-A-0409181 and J. Med. Chemistry 34, 1912 [1991], and the cholesterol-lowering and antimycotic squalestatins are described in J. Antibiotics 45, 639–647 [1992] and J. Biol. Chemistry 267, 11705–11708 [1992].

As inhibitors of the enzyme squalene epoxidase are known allylamines, such as, naftifine and terbinafine which have found their way into therapy as agents against fungal disorders, as well as the allylamine NB-598 which has antihypocholesterolaemic action (J. Biol. Chemistry 265, 18075–18078, [1990]) and fluorosqualene derivatives which have hypercholesterolaemic action (U.S. Pat. No. 5,011,859). In addition, piperidines and azadecalins with potential hypocholesterolaemic and/or antifungal activity, whose mechanism of action is not unequivocally clarified and which are squalene epoxidase and/or 2,3-epoxysqualene-lanosterol cyclase inhibitors, have been described (EP-A-0420116, EP-A-0468434, U.S. Pat. No. 5,084,461 and EP-A-0468457).

Examples of inhibitors of the enzyme 2,3-epoxysqualene-lanosterol cyclase are diphenyl derivatives (EP-A-0464465), aminoalkoxybenzene derivatives (EP-A-0410359) and piperidine derivatives (J. Org. Chem. 57, 2794–2803 [1992]), which have antifungal activity. In addition, this enzyme is inhibited in mammalian cells by decalins, azadecalins and indane derivatives (WO 80/08450, J. Biol. Chemistry 254, 11258–11263 [1981], Biochem. Pharmacology 37, 1955–1964 [1988] and JP 64/003 144), and also by 2-aza-2,3-dihydrosqualene and 2,3-epiminosqualene (Biochem. Pharmacology 34, 2765–2777 [1985]), squalenoid epoxide vinyl ethers (J. Chem. Soc. Perkin Trans. I, 1988, 461) and 29-methylidene-2,3-oxidosqualene (J. Amer. Chem. Soc. 113, 9673–9674 [1991]).

Finally, as inhibitors of the enzyme lanosterol-14α-demethylase one may also mention steroid derivatives with potential antihyperlipaemic action and which simultaneously affect the enzyme HMG-CoA reductase (U.S. Pat. No. 5,041,432, J. Biol Chemistry 266, 20070–20078 [1991], U.S. Pat. No. 5,034,548). In addition, this enzyme is inhibited by the antimycotics of the azole type as represented by N-substituted imidazoles and triazoles. This class includes, for example, the commercially available antimycotics ketoconazole and fluconazole.

The compounds of the following general formula I are novel. Surprisingly it has been found that they are very effective inhibitors of the enzyme 2,3-epoxysqualene-lanosterol cyclase (International Classification: EC5.4.99.7).

The enzyme 2,3-epoxysqualene-lanosterol cyclase catalyzes a key step in cholesterol or ergosterol biosynthesis, namely the conversion of 2,3-epoxysqualene to lanosterol, the first compound with steroid structure in the biosynthetic cascade. Compared to inhibitors of earlier biosynthetic steps, such as, for example, HMG-CoA synthase and HMG-CoA reductase, the advantage of greater selectivity can be expected from inhibitors of this enzyme, since the inhibition of the earlier biosynthetic steps leads to the decrease of biosynthetically formed mevalonic acid and as a result can also adversely affect the biosynthesis of the mevalonic acid-dependent substances dolichol, ubiquinone and isopentenyl-t-RNA (cf. J. Biol. Chemistry 265, 18075–18078 [1990]).

In the case of inhibition of biosynthetic steps after the conversion of 2,3-epoxysqualene to lanosterol, there is the risk of the accumulation of intermediate products with steroid structure in the body and the triggering of the resultant toxic effects. This is described, for example, for triparanol, a desmosterol reductase inhibitor. This substance had to be withdrawn from the market because of the formation of cataracts, ichthyosis and alopecia (cited in J. Biol. Chemistry 265, 18075–18078 [1990]).

As already stated at the beginning, inhibitors of 2,3-epoxysqualene-lanosterol cyclase are occasionally described in the literature. The structures of these compounds, however, are completely different from the structure of the compounds according to the invention of the below-mentioned general formula I.

The invention relates to the provision of antihypercholesterolaemic substances which are suitable for the treatment and prophylaxis of atherosclerosis and which, in contrast to known active compounds, are distinguished by a better antihypercholesterolaemic action and have greater selectivity and thus greater safety. Since the compounds according to the invention can also inhibit ergosterol biosynthesis in fungal organisms on account of their high activity as inhibitors of the enzyme 2,3-epoxysqualene-lanosterol cyclase, they are also suitable for the treatment of mycoses.

DETAILED DESCRIPTION OF THE INVENTION

The arylidine-1-azacycloalkanes and arylalkyl-1-azacycloalkanes of the present invention and the salts thereof have the general formula I. The compounds can optionally also be present in the form of enantiomers, diastereomers or mixtures thereof.

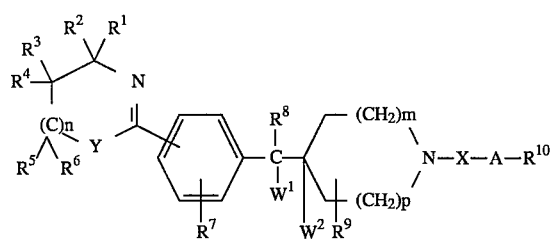

(I)

In general formula I:

n denotes the numbers 0 or 1;

m denotes the numbers 1 or 2;

p denotes the numbers 0 or 1;

A denotes a single bond, a straight-chained or branched $C_{1-17}$-alkylene group, a $C_{2-17}$-alkenylene or a $C_{2-4}$-alkynylene group;

$W^1$ and $W^2$ each denote a hydrogen atom or together denote a carbon-carbon bond;

X denotes a carbonyl or sulphonyl group;

Y denotes an oxygen or sulphur atom or an $>NR^{11}$ group;

$R^1$ to $R^6$ each denotes a hydrogen atom, or one, two or three of the groups $R^1$ to $R^6$, which groups may be identical or different, denote a straight-chained or branched $C_{1-4}$-alkyl group which may be substituted by a hydroxy, alkoxy, alkylthio or dialkylamino group or by a phenyl group which is optionally substituted by a halogen atom or an alkyl group, or denote an alkoxycarbonyl group, and the remaining groups $R^1$ to $R^6$ each denote a hydrogen atom, wherein one, two or all three of the groups $R^1$, $R^3$ and $R^5$ may also denote a phenyl group which is optionally substituted by an alkyl group or a halogen atom;

$R^7$ denotes a hydrogen or halogen atom, or an alkyl or alkoxy group, $R^8$ and $R^9$ independently of one another each denotes a hydrogen atom or an alkyl group;

$R^{10}$ denotes a hydrogen atom, a $C_{3-6}$-cycloalkyl group, or a phenyl group optionally substituted by a halogen atom, a straight-chained or branched $C_{1-4}$alkyl group, or a trifluoromethyl, alkoxy, cyano, nitro, alkylsulphonyl or phenyl group, or $R^{10}$ denotes a phenyl group substituted by two trifluoromethyl groups, by two to five halogen atoms or by a halogen atom and an alkyl group, or $R^{10}$ denotes a naphthyl or tetrahydronaphthyl group optionally substituted by a fluorine atom, or $R^{10}$ denotes a pyridyl group or a thienyl group optionally substituted by a halogen atom or an alkyl group; and $R^{11}$ denotes a hydrogen atom or an alkyl group;

wherein A cannot be a single bond if X denotes a sulphonyl group and $R^{10}$ denotes a hydrogen atom, and wherein, unless otherwise stated, the above mentioned alkyl, alkoxy, alkylthio and alkylsulphonyl groups may each contain 1 to 3 carbon atoms and the above mentioned halogen atoms may each denote a fluorine, chlorine or bromine atom.

Preferred compounds are those of the general formula Ia

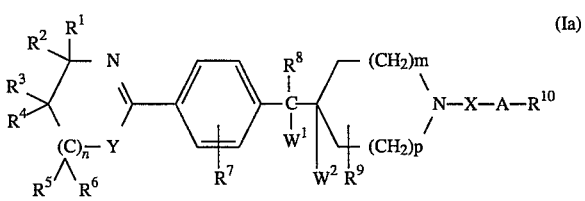

(Ia)

wherein n denotes the numbers 0 or 1;

m denotes the numbers 1 or 2;

p denotes the number 0 or 1;

A denotes a single bond, a straight-chained or branched $C_{1-17}$-alkylene group, a $C_{2-4}$-alkenylene group, or a $C_{2-4}$-alkynylene group;

$W^1$ and $W^2$ each denotes a hydrogen atom or together may denote a carbon-carbon bond;

X denotes a carbonyl or sulphonyl group;

Y denotes an oxygen or sulphur atom or an $>NR^{11}$ group;

$R^1$ to $R^4$ in each case denote a hydrogen atom or one or two of the groups $R^1$ to $R^4$ independently of one another each denote a straight-chained or branched $C_{1-4}$-alkyl group which may be substituted by a hydroxy, alkylthio or dialkylamino group or by a phenyl group itself optionally substituted by a halogen atom, or denotes a phenyl group, and the remaining groups $R^1$ to $R^4$ each denote a hydrogen atom;

$R^5$ and $R^6$, which may be identical or different, denote a hydrogen atom or a methyl group;

$R^7$ denotes a hydrogen or halogen atom, or an alkyl or alkoxy group;

$R^8$ denotes a hydrogen atom or an alkyl group;

$R^9$ denotes a hydrogen atom;

$R^{10}$ denotes a hydrogen atom, a $C_{3-6}$-cycloalkyl group, a phenyl group optionally substituted by one or two halogen atoms, by a straight-chained or branched $C_{1-4}$-alkyl group, or by a trifluoromethyl, methoxy, cyano, nitro, methylsulphonyl or phenyl group, or $R^{10}$ denotes a phenyl group substituted by two trifluoromethyl groups or by a halogen atom and a methyl group, or $R^{10}$ denotes a phenyl group substituted by three to five fluorine atoms, or $R^{10}$ denotes a naphthyl group optionally substituted by a fluorine atom, or $R^{10}$ denotes a tetrahydronaphthyl or pyridyl group, or a thienyl group optionally substituted by a halogen atom; and $R^{11}$ denotes a hydrogen atom or an alkyl group;

wherein A cannot be a single bond if X denotes a sulphonyl group and $R^{10}$ denotes a hydrogen atom, and wherein, unless otherwise stated, the above mentioned alkyl groups may each contain 1 to 3 carbon atoms and the above mentioned halogen atoms may each denote a fluorine, chlorine or bromine atom, and the enantiomers, diastereomers and salts thereof.

Particularly preferred compounds are those of the general formula Ia,
wherein:

n denotes the numbers 0 or 1;

m denotes the numbers 1 or 2;

p denotes the numbers 0 or 1;

A denotes a single bond, a straight-chained or branched $C_{1-17}$-alkylene group, a $C_{2-4}$-alkenylene group;

$W^1$ and $W^2$ each denote a hydrogen atom or together denote a carbon-carbon bond;

X denotes a carbonyl or sulphonyl group;

Y denotes an oxygen atom or an $>NR^{11}$ group;

$R^1$ to $R^4$ in each case denote a hydrogen atom, or one or two of the groups $R^1$ to $R^4$ independently of one another each denote a straight-chained or branched $C_{1-4}$-alkyl group, and the remaining groups $R^1$ to $R^4$ each denote a hydrogen atom;

$R^5$ and $R^6$, which may be identical or different, denote a hydrogen atom or a methyl group;

$R^7$ denotes a hydrogen or halogen atom, or a methyl or methoxy group;

$R^8$ denotes a hydrogen atom or a methyl group;

$R^9$ denotes a hydrogen atom;

$R^{10}$ denotes a hydrogen atom, a $C_{3-6}$-cycloalkyl group a phenyl group optionally substituted by one or two halogen atoms, by five fluorine atoms, by an alkyl group, by one or two trifluoromethyl groups or by a halogen atom and an alkyl group, or $R^{10}$ denotes a 1-naphthyl group which is optionally substituted in the 4-position by a fluorine atom, or $R^{10}$ denotes a 2-naphthyl group, a 1,2,3,4-tetrahydro-2-naphthyl group, a pyridyl or 4-biphenyl group or a thienyl group optionally substituted by a halogen atom; and $R^{11}$ denotes a hydrogen atom or a methyl group;

wherein A cannot be a single bond if X denotes the sulphonyl group and $R^{10}$ denotes a hydrogen atom, and wherein, unless otherwise stated, the above mentioned alkyl moieties may each contain 1 to 3 carbon atoms and the above mentioned halogen atoms may each denote a fluorine or chlorine atom, and the enantiomers, diastereomers and salts thereof.

Especially particularly preferred compounds are those of the general formula Ia,
wherein:

n denotes the numbers 0 or 1;

m denotes the number 1;

p denotes the numbers 0 or 1;

A denotes a single bond;

$W^1$ and $W^2$ each denote a hydrogen atom or together denote a carbon-carbon bond;

X denotes a carbonyl group;

Y denotes an oxygen atom;

$R^1$ to $R^6$ in each case denote a hydrogen atom;

$R^7$ denotes a hydrogen or halogen atom or a methyl group;

$R^8$ and $R^9$ each denote a hydrogen atom;

$R^{10}$ denotes a phenyl group substituted in the 4-position by a fluorine, chlorine or bromine atom or by a trifluoromethyl group, or $R^{10}$ denotes a 4-chloro-3-methylphenyl group, a 5-chloro-2-thienyl group or a cyclohexyl group;

and the salts thereof, but in particular the compounds (1) 1-(4-chlorobenzoyl)-4-[4-(2-oxazolin-2-yl)benzylidene] piperidine (2) 1-(4-chlorobenzoyl)-4-[4-(4,5-dihydro-6H-oxazin-2-yl)benzylidene] piperidine (3) 4-[4-(2-oxazolin-2-yl)benzylidene]-1-(4-trifluoromethylbenzoyl)piperidine (4) 1-(4-chloro-3-methylbenzoyl)-4-[4-(2-oxazolin-2-yl)benzylidene] piperidine (5) 1-(4-fluorobenzoyl)-4-[4-(2-oxazolin-2-yl)benzylidene] piperidine (6) 1-(5-chloro-2-thienoyl)-4-[4-(2-oxazolin-2-yl)benzylidene] piperidine (7) 1-cyclohexanecarbonyl-4-[4-(2-oxazolin-2-yl)benzylidene] piperidine (8) 4-[4-(2-oxazolin-2-yl)benzyl]-1-(4-trifluoromethylbenzoyl)piperidine (9) 1-(4-chlorobenzoyl)-4-[4-(2-oxazolin-2-yl)benzyl]piperidine

(10) 1-(4-chlorobenzoyl)-3-[4-(2-oxazolin-2-yl)benzylidene] pyrrolidine

(11) 1-(4-chlorobenzoyl)-4-[2-fluoro-4-(2-oxazolin-2-yl)benzylidene] piperidine

(12) 1-(4-chlorobenzoyl)-4-[3-methyl-4-(2-oxazolin-2-yl)benzylidene] piperidine and the salts thereof.

Preparation methods:

The compounds of the general formula I may be prepared by the following methods:

a) By reaction of compounds of the general formula II

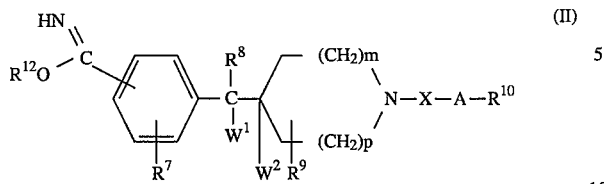

(wherein m, p, A, $W^1$, $W^2$, X and $R^7$ to $R^{10}$ are as hereinbefore defined and $R^{12}$ denotes a $C_{1-10}$-alkyl group) with compounds of the general formula III

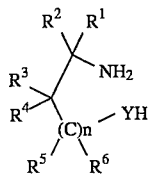

wherein n, Y and $R^1$ to $R^6$ are as hereinbefore defined.

The reactions are appropriately carried out in a suitable solvent, e.g. in an alcohol such as methanol, ethanol or propanol, in an ether such as, for example, diethyl ether, di-n-propyl ether, tetrahydrofuran or dioxane, in dimethylformamide, dimethylsulphoxide or in a mixture of the above mentioned solvents, optionally in the presence of a hydrogen halide-binding agent such as a tertiary amine, sodium carbonate or calcium carbonate, at a temperature between 0° and 100° C. The reaction is preferably carried out, however, in an alcohol such as methanol or ethanol at a temperature between 20° and 80° C. Advantageously, the compounds of the general formula II are used as salts, preferably as hydrochlorides, and the reaction is carried out in the presence of inorganic or organic bases, preferably tertiary organic amines such as triethylamine or ethyldiisopropylamine or an excess of the compound of the general formula III.

b) For the preparation of compounds of the general formula I, wherein n, m, p, A, X, Y and $R^1$ to $R^{10}$ are as hereinbefore defined and $W^1$ and $W^2$ together denote a carbon-carbon bond:

Reaction of phosphonate esters of the general formula IV

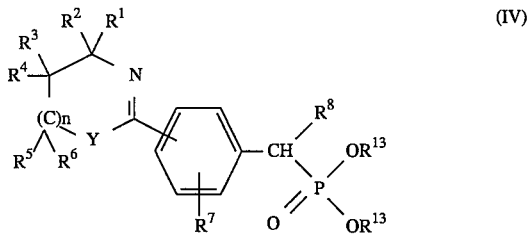

(wherein n, Y and $R^1$ to $R^8$ are as hereinbefore defined and $R^{13}$ denotes a $C_{1-10}$-alkyl group) with compounds of the general formula V

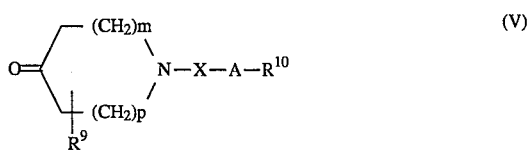

wherein m, p, A, X, $R^9$ and $R^{10}$ are as hereinbefore defined.

The reactions are conveniently carried out in a suitable solvent, e.g. in an ether such as diethyl ether, di-n-propyl ether, tetrahydrofuran or dioxane, or in a hydrocarbon such as, for example, benzene, toluene, n-hexane or cyclohexane, or in a mixture of the above mentioned solvents, but preferably in a mixture of tetrahydrofuran and n-hexane or a mixture of tetrahydrofuran and cyclohexane. In this reaction, the compounds of the general formula IV are first converted into the corresponding phosphonate anions at a temperature between −78° and 20° C. using a suitable base such as, for example, n-butyllithium, phenyllithium, sodium amide, sodium hydride or lithium diisopropylamide and these are then reacted with the compounds of the general formula V at a temperature between −78° and 100° C., but preferably at a temperature between −15° and 50° C.

If a compound of the general formula IV has a hydroxy group, it is recommended to protect this with a suitable protecting group such as, for example, the silyl group, before carrying out the reaction and to remove the protecting group again, after the reaction is complete. A suitable silylation reagent is e.g. trimethylchlorosilane. Removal may be carried out, for example, by means of acidic hydrolysis or by treatment with fluoride ions, e.g. with caesium fluoride or tetrabutylammonium fluoride.

c) By reaction of compounds of the general formula VI

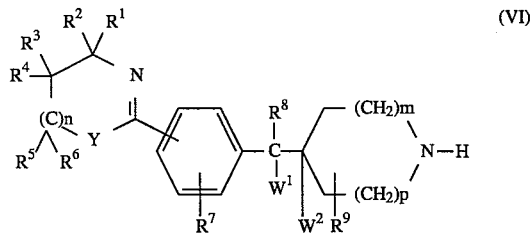

(wherein n, m, p, $W^1$, $W^2$, Y and $R^1$ to $R^9$ are as hereinbefore defined)

With compounds of the general formula VII

wherein A, X and $R^{10}$ are as hereinbefore defined and $Z^1$ denotes a reactive leaving group such as e.g. a halogen atom, preferably a chlorine atom, or the imidazolide group.

If $Z^1$ denotes a halogen atom, the reactions are carried out in a suitable inert solvent such as diethyl ether, toluene, methylene chloride and the like, preferably at temperatures between −50° C. and 50° C. and in the presence of a hydrogen halide-binding agent, such as a tertiary amine, sodium carbonate or calcium carbonate. In this reaction, not only may the free amines of the general formula VI be employed, but also their salts, from which the amines may be released in situ by suitable bases, e.g. tertiary organic amines.

If $Z^1$ denotes the imidazolide group, the reactions are preferably carried out in an inert solvent, such as xylene or tetrahyrofuran, at temperatures between ambient temperature and the boiling point of the reaction mixture.

If a compound of the general formula VI has a hydroxy group, the reaction may be modified such that two equivalents of the compound of the general formula VII are used and, after the reaction is complete, the ester group formed from the hydroxy group is hydrolyzed again.

The subsequent optional hydrolysis of an ester group formed in this way is preferably carried out by alkaline hydrolysis in an aqueous solvent, e.g. in water, isopropanol/water, tetrahydrofuran/water or dioxane/water, for example in the presence of an alkali base such as sodium hydroxide or potassium hydroxide at temperatures between 0° and 100° C.

d) For the preparation of compounds of the general formula I wherein n, m, p, X and $R^7$ to $R^9$ are as hereinbefore defined, A denotes a single bond or a straight-chained or

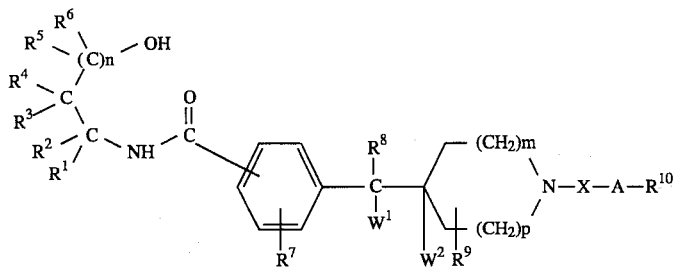

branched $C_{1-17}$-alkylene group, $W^1$ and $W^2$ each denote a hydrogen atom, Y denotes an oxygen atom or the $>NR^{11}$ group wherein $R^{11}$ is as hereinbefore defined, $R^1$ to $R^6$ are as hereinbefore defined with the exception of the straight-chained or branched $C_{1-4}$-alkyl group substituted by an alkylthio group, and $R^{10}$ is as hereinbefore defined with the exception of the thienyl group optionally substituted by a halogen atom, and wherein A cannot be a single bond if X denotes the sulphonyl group and $R^{10}$ denotes a hydrogen atom:

Hydrogenation of a compound of the general formula I'

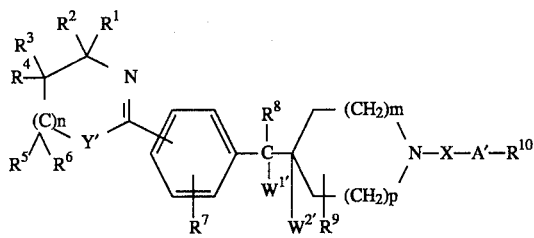

wherein n, m, p, X and $R^7$ to $R^9$ are as hereinbefore defined, A' denotes a single bond or a straight-chained or branched $C_{1-17}$-alkylene group, $W^{1'}$ and $W^{2'}$ together denote a carbon-carbon bond, Y' denotes an oxygen atom or the $>NR^{11}$ group wherein $R^{11}$ is as hereinbefore defined, $R^1$ to $R^6$ are as hereinbefore defined with the exception of the straight-chained or branched $C_{1-4}$-alkyl group substituted by an alkylthio group, and $R^{10}$ is as hereinbefore defined with the exception of the thienyl group optionally substituted by a halogen atom, and wherein A cannot be a single bond if X denotes the sulphonyl group and $R^{10}$ denotes a hydrogen atom.

The hydrogenation is carried out in a suitable solvent such as in an alcohol, for example in methanol, ethanol or propanol, in an ester, for example in ethyl acetate, in an ether, for example, in diethyl ether, tetrahydrofuran or dioxane, or a mixture thereof, with catalytically activated hydrogen, e.g. with hydrogen in the presence of a hydrogenation catalyst such as Raney-nickel, rhodium, palladium, palladium/carbon, platinum or platinum/carbon and a hydrogen pressure of 10 to 500 psi, but preferably 50 to 100 psi, at temperatures between 0° and 100° C., but preferably at ambient temperature.

In the above hydrogenation, a halogen atom present in the groups $R^1$ to $R^6$ and $R^{10}$ may optionally be replaced by a hydrogen atom.

e) For the preparation of compounds of the general formula I wherein n, m, p, A, X, $W^1$, $W^2$ and $R^1$ to $R^{10}$ are as hereinbefore defined and Y denotes an oxygen atom:

Cyclization of compounds of the general formula VIII (VIII)

wherein n, m, p, A, X, $W^1$, $W^2$, and $R^1$ to $R^{10}$ are as hereinbefore defined.

The cyclization is conveniently carried out in a suitable solvent, e.g. in diethyl ether, tetrahydrofuran, dioxane, diethylene glycol dimethyl ether, methylene chloride, chloroform, benzene, toluene or n-hexane or in a mixture of the above mentioned solvents in the presence of a dehydrating agent such as the combination dialkyl azodicarboxylate and triphenylphosphine, or of methyl-N-(triethylammoniosulphonyl)carbamate (Burgess reagent), at a temperature between 0° and 150° C., preferably at a temperature between 0° and 100° C. The use of the Burgess reagent for the preparation of oxazolines is described in Tetrahedron Letters 33, 907–910 [1992]. A further cyclization method is described in Tetrahedron Letters 33, 2807–2810 [1992].

The compounds of the general formula I prepared by the above processes may be purified and isolated by known methods e.g. crystallization, distillation or chromatography. They may be converted into their acid addition salts with inorganic or organic acids by methods known per se.

In the compounds of the formula I according to the invention, depending on the nature of the groups $R^1$ to $R^6$, the carbon atoms connected to these groups may be present in an optically active form. The invention includes both the pure isomers and the mixtures of the different isomers.

Starting Materials:

The starting compounds of the general formula II may be prepared from compounds of the general formula IX (wherein m, p, A, $W^1$, $W^2$, X and $R^7$ to $R^{10}$ are as hereinbefore defined and D represents a cyano group) by reaction with

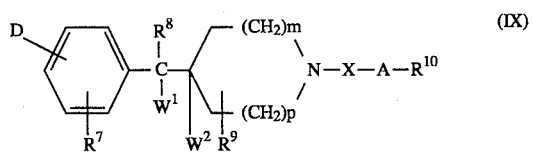

alcohols of the formula $R^{12}OH$ (wherein $R^{12}$ denotes a $C_{1-10}$-alkyl group) in the presence of hydrogen chloride.

Compounds of the formula IX wherein D represents a cyano or alkoxycarbonyl group are in turn obtainable by reaction of phosphonate esters of the formula X

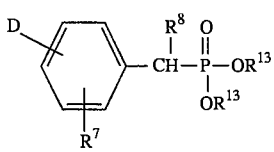 (X)

(wherein $R^7$ and $R^8$ are as hereinbefore defined, $R^{13}$ represents a $C_{1-10}$-alkyl group and D represents a cyano or alkoxycarbonyl group) with ketones of the formula V

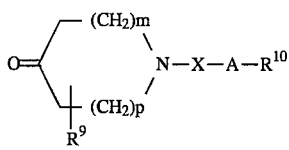 (V)

(wherein m, p, A, X, $R^9$ and $R^{10}$ are as hereinbefore defined) in the presence of bases such as, for example, n-butyllithium, phenyllithium, sodium amide, sodium hydride or lithium diisopropylamide and, if appropriate, with subsequent hydrogenation of the olefinic double bond thus obtained.

An alternative method for the preparation of compounds of the formula IX (wherein m, p, A, $W^1$, $W^2$, X and $R^7$ to $R^{10}$ are as hereinbefore defined and D denotes an alkoxycarbonyl or cyano group) consists of reacting phosphonate esters of the formula X (wherein $R^7$, $R^8$ and $R^{13}$ are as hereinbefore defined and D denotes an alkoxycarbonyl or cyano group) with ketones of the formula XI

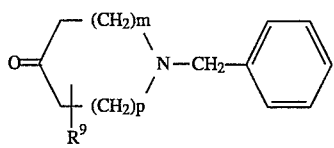 (XI)

wherein m, p, and $R^9$ are as hereinbefore defined.

The benzyl group is then removed, for example by reaction with 1-chloroethyl chloroformate, the urethane thus formed is cleaved with methanol and finally reacted with compounds of the general formula VII

 $Z^1-X-A-R^{10}$ (VII)

wherein A, X and $R^{10}$ are as hereinbefore defined and $Z^1$ denotes a reactive leaving group such as e.g. a halogen atom, preferably a chlorine atom, or the imidazolide group.

The olefinic double bond may subsequently be hydrogenated if desired.

The phosphonate esters of the formula X may be prepared by Arbusow reaction from halides of the formula XII

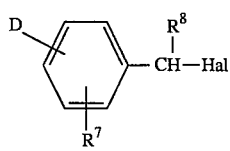 (XII)

(wherein $R^7$ and $R^8$ are as hereinbefore defined, D represents a cyano or alkoxycarbonyl group and Hal denotes a halogen atom such as, for example, a chlorine or bromine atom) and trialkyl phosphites of the formula $(R^{13}O)_3P$, in which $R^{13}$ is as hereinbefore defined. A preferred variant of the reaction for the preparation of compounds of the formula X wherein $R^8$ denotes an alkyl group consists of first preparing compounds of the formula X in which $R^8$ denotes a hydrogen atom, and then reacting these with an alkylating agent of the formula $R^8-Z^2$ wherein $R^8$ denotes an alkyl group as hereinbefore defined and $Z^2$ denotes a halogen atom such as a chlorine, bromine or iodine atom or a sulphonyloxy group.

The starting compounds of the general formulae III and XII are known from the literature or may be prepared by known methods.

The phosphonate esters of the general formula IV may be obtained from phosphonate esters of the general formula XIII

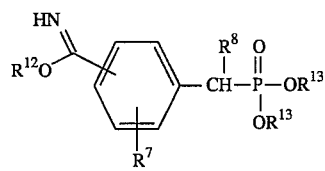 (XIII)

(wherein $R^7$, $R^8$ and $R^{12}$ are as hereinbefore defined and $R^{13}$ denotes a $C_{1-10}$-alkyl group) by reaction with compounds of the general formula III.

The phosphonate esters of the formula XIII are obtainable from the phosphonate esters of the formula X wherein D denotes a cyano group, by reaction with alcohols of the formula $R^{12}OH$ wherein $R^{12}$ is as hereinbefore defined, in the presence of hydrogen chloride.

The compounds of the general formula V are obtained by reaction of compounds of the formula XIV,

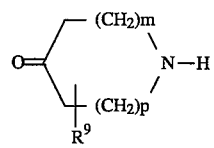 (XIV)

(wherein m, p and $R^9$ are as hereinbefore defined), with compounds of the general formula VII.

The starting compounds of the general formula VI may be prepared from the phosphonate esters of the general formula IV by reaction with compounds of the general formula XV

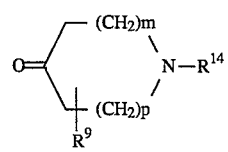 (XV)

(wherein m, p and $R^9$ are as hereinbefore defined and $R^{14}$ denotes the triphenylmethyl or tert.butoxycarbonyl group) in the presence of strong bases such as n-butyllithium, phenyllithium, sodium amide, sodium hydride or lithium diisopropylamide and optionally with subsequent catalytic hydrogenation of the olefinic double bond formed and removal of the group $R^{14}$ (defined as above) by means of trifluoroacetic acid, wherein in the case of the triphenylmethyl compound, this protecting group may be removed simultaneously by hydrogenolysis.

An alternative method for the preparation of compounds of the general formula VI wherein p denotes the number 0, m denotes the number 1 and $R^8$ denotes a hydrogen atom and n, $W^1$, $W^2$, Y, $R^1$ to $R^7$ and $R^9$ are as hereinbefore defined, consists of first condensing a compound of the formula XVI

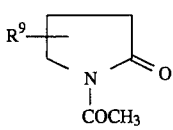

(wherein $R^9$ is as hereinbefore defined with an aldehyde of the formula XVII

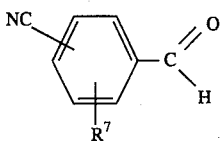

(wherein $R^7$ is as hereinbefore defined) with simultaneous removal of the n-acetyl group, then reacting with an alcohol of the formula $R^{12}OH$ (wherein $R^{12}$ represents a $C_{1-10}$-alkyl group) under the influence of hydrogen chloride, and cyclizing the intermediate product thus obtained with a compound of the formula III

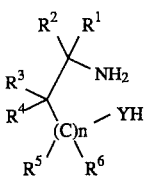

wherein n, Y and $R^1$ to $R^5$ are as hereinbefore defined. The amide group is then reduced, for example using lithium aluminium hydride and, if desired, the olefinic double bond is hydrogenated.

Starting compounds of the general formula VIII may be prepared from compounds of the general formula IX (wherein m, p, $W^1$, $W^2$, X, A and $R^7$ to $R^{10}$ are as hereinbefore defined and D denotes an alkoxycarbonyl group) by hydrolysis of the alkoxycarbonyl group and reaction of the resulting carboxylic acid first with N,N'-carbonyldiimidazole and then with compounds of the formula III wherein n and $R^1$ to $R^6$ are as hereinbefore defined and Y represents an oxygen atom.

The compounds of the general formula I have interesting biological properties. They are inhibitors of cholesterol biosynthesis, in particular inhibitors of the enzyme 2,3-epoxysqualene lanosterol cyclase. On account of their biological properties, they are particularly suitable for the treatment and prophylaxis of hyperlipidaemias, in particular of hypercholesterolaemia, hyperlipoproteinaemia and hypertriglycerideaemia and the atherosclerotic vascular changes resulting therefrom and their sequelae such as coronary heart disease, cerebral ischaemia, intermittent claudication, gangrene and others.

For the treatment of these disorders, the compounds of the general formula I may either be employed on their own for monotherapy or used with other cholesterol- or lipid-lowering substances, wherein the compounds may preferably be administered as an oral formulation, and optionally also in the form of suppositories as a rectal formulation. Possible combination components in this case are, for example:

bile acid-binding resins such as e.g. cholestyramine, colestipol, etc., compounds which inhibit cholesterol absorption, such as e.g. sitosterol and neomycin, compounds which intervene in cholesterol biosynthesis, such as e.g. HMG-CoA reductase inhibitors such as lovastatin, simvastatin, pravastatin, etc., squalene epoxidase inhibitors such as, for example, NB 598 and analogous compounds and also squalene synthetase inhibitors such as, for example, representatives of the isoprenoid-(phosphinylmethyl)phosphonate class and squalestatin.

Further possible combination components which may be mentioned are the fibrate class, such as clofibrate, bezafibrate, gemfibrozil, etc., and nicotinic acid, its derivatives and analogues such as, for example, acipimox and probucol.

In addition, the compounds of the general formula I are suitable for the treatment of disorders which are connected with excessive cell proliferation. Cholesterol is an essential cell constituent and must be present in an adequate amount for cell proliferation, i.e. cell division. The inhibition of cell proliferation by inhibition of cholesterol biosynthesis is illustrated by the example of smooth muscle cells with the HMG-CoA reductase inhibitor of the mevinolin type lovastatin, as mentioned at the beginning.

Foremost examples of disorders which are connected with excessive cell proliferation are carcinoses. In cell culture and in in vivo experiments, it has been shown that lowering of the serum cholesterol or intervention in cholesterol biosynthesis by HMG-CoA reductase inhibitors reduces tumour growth (Lancet 339, 1154–1156 [1992]). The compounds of the formula I according to the invention are therefore potentially suitable for the treatment of carcinoses on account of their cholesterol biosynthesis-inhibitory activity. They may be used for this purpose on their own or to support known therapy principles.

Further examples which may be mentioned are hyperproliferative skin disorders such as, for example, psoriasis, basal cell carcinoma, squamous cell carcinoma, keratosis and keratinization disorders. The expression "psoriasis" used here, signifies a hyperproliferative-inflammatory skin disorder which changes the regulation mechanism of the skin. In particular, lesions are formed which include primary and secondary changes of proliferation in the epidermis, inflammatory reactions of the skin and the expression of regulatory molecules such as lymphokines and inflammation factors. Psoriatic skin is morphologically characterized by an increased turnover of epidermis cells, thickened epidermis, abnormal keratinization of inflammatory cell infiltrates into the dermis layer and polymorphonuclear leucocyte infiltration into the epidermis, which causes an increase in the basal cell cycle. Hyperkeratotic and parakeratotic cells are also present. The expressions "keratosis", "basal cell carcinoma", "squamous cell carcinoma" and "keratinization disorders" relate to hyperproliferative skin disorders in which the regulation mechanism for the proliferation and differentiation of the skin cells is interrupted.

The compounds of the formula I are active as antagonists of skin hyperproliferation, i.e. as agents which inhibit the hyperproliferation of human keratinocytes. As a result of this, the compounds are suitable as agents for the treatment of hyperproliferative skin disorders such as psoriasis, basal cell carcinomas, keratinization disorders and keratosis. For the treatment of these disorders, the compounds of the formula I may be administered either orally or topically, and they may be used either on their own in a form of monotherapy or in combination with known active compounds.

Further noteworthy examples are hyperproliferative vascular disorders such as stenoses and vascular occlusions caused by surgical measures such as PTCA (percutaneous transluminal coronary angioplasty) or bypass operations, which are based on the proliferation of smooth muscle cells. As mentioned at the beginning, it is known that this cell proliferation can be suppressed by HMG-CoA reductase inhibitors of the mevinolin type, such as lovastatin. On account of their inhibitory effect on cholesterol biosynthesis, the compounds of the general formula I are also suitable for the treatment and prophylaxis of these disorders, where they may either be used on their own or in combination with known active compounds, such as e.g. intravenously administered heparin, preferably in oral administration.

A further possible use of the compounds of the general formula I according to the invention is the prophylaxis and treatment of gallstone trouble. The formation of gallstones is caused by the cholesterol concentration in the bile exceeding the maximum solubility of cholesterol in the bile fluid, causing precipitation of the cholesterol in the form of gallstones. Hypolypidaemic agents of the fibrate class lead to an increased secretion of neutral steroids via the bile and increase the susceptibility to gallstone formation.

In contrast to this, cholesterol biosynthesis inhibitors such as lovastatin or pravastatin do not lead to increased gallstone formation, but can cause a reduction of the cholesterol concentration in the bile and thus reduce the so-called lithogenic index, a measure of the probability of gallstone formation. This is described in Gut 31, 348–350 [1990] and in Z. Gastroenterol. 29, 242–245 [1991].

Moreover, the effectiveness of lovastatin in the disolution of gallstones, in particular in combination with ursodeoxycholic acid, is described in Gastroenterology 102, No. 4, Pt. 2, A 319 [1992]. On account of their mode of action, the compounds of the general formula I are therefore also of importance for the prophylaxis and treatment of gallstone trouble. They may be used either on their own or in combination with known therapies such as, for example, treatment with ursodeoxycholic acid or shock wave lithotripsy, preferably by oral administration.

Finally, the compounds of the general formula I are suitable for the therapy of infections due to pathogenic fungi such as e.g. *Candida albicans, Aspergillus niger, Trichophyton mentagrophytes, Penicillium sp., Cladosporium sp.,* etc. As previously mentioned, the final product of sterol biosynthesis in the fungal organism is not cholesterol, but ergosterol which is essential for the integrity and function of the fungal cell membranes. The inhibition of ergosterol biosynthesis therefore leads to growth disorders and possibly to the destruction of the fungal organisms.

For the treatment of mycoses, the compounds of the general formula I may either be administered orally or topically. They may be employed either on their own or in combination with known antimycotic active compounds, in particular with those which intervene in other stages of sterol biosynthesis, such as, for example, the squalene epoxidase inhibitors terbinafine and naftifine or the lanosterol 14α-demethylase inhibitors of the azole type such as, for example, ketoconazole and fluconazole.

A further possible use of the compounds of the general formula I relates to an application in raising poultry. The lowering of the cholesterol content of eggs by administration of the HMG-CoA reductase inhibitor lovastatin in laying hens has been described (FASEB Journal 4, A 533, Abstracts 1543 [1990]). The production of low-cholesterol eggs is of interest, since the cholesterol loading of the body may be decreased without a change in feeding habits by eggs with a reduced cholesterol content. As a result of their inhibitory effect on cholesterol biosynthesis, the compounds of the general formula I may also be used in poultry breeding for the production of low-cholesterol eggs, the substances preferably being administered to the feed as additives.

The biological activity of compounds of the general formula I was determined by the following methods:

I. Measurement of the inhibition of $^{14}C$-acetate incorporation in digitonin-precipitatable steroids:

Method:

After 3 days of culture, human hepatoma cells (HEP-G2) are stimulated for 16 hours in cholesterol-free medium. The substances to be tested (dissolved in dimethyl sulphoxide, final concentration 0.1%) are added during this stimulation phase. After the addition of 200 μmol/l of 2-$^{14}C$-acetate, the mixture is then reincubated at 37° C. for a further 2 hours.

The cells are detached and the sterol esters are hydrolyzed and, after extraction, sterols are precipitated using digitonin. The $^{14}C$-acetate incorporated into digitonin-precipitatable sterols is determined by scintillation measurement.

The investigation of the inhibitory action was carried out at test concentrations of $10^{-7}$ mol/l and $10^{-8}$ mol/l. The test results of the following compounds A to AG of the general formula I are indicated at these test concentrations by way of example:

A=1-(4-chlorobenzoyl)-4-[4-(2-oxazolin-2-yl)benzylidene] piperidine
B=1-(4-chlorobenzoyl)-4-[4-(4,5-dihydro-6H-oxazin-2-yl)benzylidene] piperidine
C=4-[4-(2-oxazolin-2-yl)benzylidene]-1-(4-trifluoromethylbenzoyl)piperidine
D=1-(4-chloro-3-methylbenzoyl)-4-[4-(2-oxazolin-2-yl)benzylidene] piperidine
E=1-(4-fluorobenzoyl)-4-[4-(2-oxazolin-2-yl)benzylidene] piperidine
F=1-(5-chloro-2-thienoyl)-4-[4-(2-oxazolin-2-yl)benzylidene] piperidine
G=1-cyclohexanecarbonyl-4-[4-(2-oxazolin-2-yl)benzylidene] piperidine
H=4-[4-(2-oxazolin-2-yl)benzyl]-1-(4-trifluoromethylbenzoyl)piperidine
I=1-(4-chlorobenzoyl)-4-[4-(2-oxazolin-2-yl)benzyl] piperidine
K=1-(4-chlorobenzoyl)-3-[4-(2-oxazolin-2-yl)benzylidene] pyrrolidine
L=1-(4-chlorobenzoyl)-4-[2-fluoro-4-(2-oxazolin-2-yl)benzylidene] piperidine
M=1-(4-chlorobenzoyl)-4-[3-methyl-4-(2-oxazolin-2-yl)benzylidene] piperidine
N=1-(4-chlorobenzenesulphonyl)-4-[4-(2-oxazolin-2-yl)benzylidene] piperidine
O=1-(4-chlorobenzenesulphonyl)-4-[4-(2-imidazolin-2-yl)benzylidene] piperidine
P=1-(4-chlorobenzoyl)-4-[4-(2-thiazolin-2-yl)benzyl]piperidine
Q=1-(4-chlorobenzoyl)-4-[4-(S-5-methyl-2-oxazolin-2-yl)benzylidene] piperidine
R=1-(4-chlorobenzoyl)-4-[4-(R-4-methyl-2-oxazolin-2-yl)benzylidene] piperidine
S=1-(4-chlorobenzoyl)-4-[4-(5-phenyl-2-oxazolin-2-yl)benzylidene] piperidine
T=1-(4-chlorobenzoyl)-4-[4-(5-diethylaminomethyl-2-oxazolin- 2-yl)benzylidene]piperidine
U=1-(4-chlorobenzoyl)-4-[4-(4-hydroxymethyl-2-oxazolin-2-yl)benzylidene]piperidine
V=4-[4-(S-4-benzyl-2-oxazolin-2-yl)benzylidene]-1-(4-chlorobenzoyl)piperidine
W=1-(4-chlorobenzoyl)-4-[4-(2-oxazolin-2-yl)-α-methylbenzylidene] piperidine
X=1-(5-chloro-2-thienoyl)-4-[4-(2-oxazolin-2-yl)benzylidene] piperidine
Y=1-(4-cyanobenzoyl)-4-[4-(2-oxazolin-2-yl)benzylidene] piperidine Z=4-[4-(2-oxazolin-2-yl)benzylidene]-1-(pentafluorobenzoyl)piperidine
AA=1-benzoyl-4-[4-(2-oxazolin-2-yl)benzylidene]piperidine
AB=1-(4-tert.butylbenzoyl)-4-[4-(2-oxazolin-2-yl)benzylidene]piperidine
AC=1-(4-methoxybenzoyl)-4-[4-(2-oxazolin-2-yl)benzylidene] piperidine
AD=1-(4-bromobenzoyl)-4-[4-(2-oxazolin-2-yl)benzylidene] piperidine
AE=1-(4-nitrobenzoyl)-4-[4-(2-oxazolin-2-yl)benzylidene] piperidine
AF=1-(4-chlorophenylacetyl)-4-[4-(2-oxazolin-2-yl)benzylidene] piperidine
AG=1-(1-naphthylcarbonyl)-4-[4-(2-oxazolin-2-yl)benzylidene] piperidine The percentage values by which the above compounds inhibit $^{14}C$-acetate incorporation are indicated in the following Table:

| Mol/l | $10^{-7}$ | $10^{-8}$ |
|---|---|---|
| A | −81 | −58 |
| B | −77 | −51 |
| C | −90 | −74 |
| D | −88 | −55 |
| E | −81 | −36 |
| F | −84 | −55 |
| G | −80 | −45 |
| H | −86 | −62 |
| I | −89 | −75 |
| K | −90 | −56 |
| L | −83 | −52 |
| M | −76 | −32 |
| N | −86 | −63 |
| O | −45 | −1 |
| P | −14 | −5 |
| Q | −89 | −44 |
| R | −88 | −57 |
| S | −24 | 0 |
| T | −57 | −29 |
| U | −60 | −21 |
| V | −29 | −15 |
| W | −77 | −35 |
| X | −84 | −35 |
| Y | −74 | −51 |
| Z | −45 | −8 |
| AA | −70 | −25 |
| AB | −18 | −6 |
| AC | −25 | −16 |
| AD | −85 | −44 |
| AE | −71 | −22 |
| AF | −63 | −22 |
| AG | −67 | −30 |

As mentioned previously, inhibitors of the enzyme 2,3-epoxysqualene-lanosterol cyclase are occasionally described in the literature, however, in terms of their structure these differ very greatly from the compounds of the formula I according to the invention. The compounds structurally most closely related to the compounds of the general formula I are described in EP 0468457 A1. For comparison, therefore, Example 1 of this publication was tested by the determination method described above with test concentrations of $10^{-5}$ mol/l and $10^{-6}$ mol/l. The inhibitory values of 41% and 13% found here, show that these compounds are clearly inferior to the compounds of the general formula I according to the invention.

II. Measurement of the in vivo effect in the rat after oral administration

The inhibition of the enzyme 2,3-epoxysqualene-lanosterol cyclase causes an increase in the 2,3-epoxy-squalene level in the liver and plasma. Therefore, the amount of 2,3-epoxysqualene formed therefore serves as a direct measure of the effectiveness in the whole animal. The determination is carried out by the following method:

The test substance suspended in 1.5% strength aqueous methylcellulose is administered via stomach tube to male Wistar rats (160–190 g body weight). 5 hours after administration, blood is obtained retroorbitally from the venous plexus. Plasma is extracted by the method of Bligh and Dyer (Canad. J. Biochem. Physiol. 37, 912, [1959]), purified by means of a precolumn and then analyzed by means of HPLC. The peaks obtained are identified and quantified by means of calibration substances. An internal standard is used to check the reproducibility of the results.

The investigations were carried out using concentrations of 0.1 and 1.0 mg/kg. The results for the above mentioned substances A to M are compiled in the following Table by way of example:

| | 2,3-Epoxysqualene concentration (µg/ml) in plasma (rat) | |
|---|---|---|
| mg/kg | 0.1 | 1.0 |
| A | 0.71 | 3.75 |
| B | 0.46 | 3.14 |
| C | 0.91 | 5.90 |
| D | 0.78 | 3.35 |
| E | 0.67 | 6.09 |
| F | 0.00 | 2.00 |
| G | 0.36 | 0.31 |
| H | 1.70 | 9.15 |
| I | 3.41 | 8.41 |
| K | 0.0 | 4.14 |
| L | 0.44 | 6.46 |
| M | 0.78 | 6.53 |

Measurable 2,3-epoxysqualene levels did not occur in the control animals under the experimental conditions.

To date, none of the inhibitors of the enzyme 2,3-epoxysqualene-lanosterol cyclase as described in the literature have been attributed with inhibitory activity against cholesterol biosynthesis in the whole animal.

III. Lipid reduction in the normolipaemic golden hamster

Male golden hamsters are fed ad lib with a cholesterol-free hamster diet for 12 days. The substance to be tested is admixed to the feed in concentrations of 0.01 to 0.10%. At the end of the experimental period, the total cholesterol, the HDL fraction and also the VLDL+LDL fraction are determined by standard methods, a control group fed without test substance being used for comparison.

The hypolipidaemic activity of the above mentioned compound A was tested. The results are compiled in the following Table:

| Concentration | Total Cholesterol | VLDL + LDL | HDL |
|---|---|---|---|
| 0.01% | −19.8% | −25.0% | −12.4% |
| 0.03% | −26.3% | −31.2% | −17.5% |
| 0.10% | −25.8% | −36.6% | −13.9% |

IV. Determination of the lithogenic index in the normolipaemic golden hamster

The lithogenic index is a measure of susceptibility to gallstone formation and is defined as the quotient of the maximum equilibrium solubility of cholesterol at the existing bile acid and phospholipid concentration and the actual cholesterol content in mol %. It was determined by the method of Carey and Small, described in J. Clin. Investig.

61, 998–1026 [1978]. The higher the lithogenic index, the higher the probability of gallstone formation. The determination of the lithogenic index was carried out as follows:

Male golden hamsters are fed ad lib with a cholesterol-free hamster diet for 20 days. The substance to be tested is admixed to the feed in concentrations of 0.01 to 0.1%. At the end of the experimental period, total cholesterol, the HDL fraction and also the VLDL+LDL fraction in the serum, and the bile acids, the cholesterol and the phospholipids in the bile are determined by standard methods.

The compound A described above was tested. The percentage decrease in the lithogenic index was determined relative to the control. The results are compiled in the following Table.

| Concentration | Lithogenic Index |
|---|---|
| 0.01% | −24% |
| 0.03% | −10% (n.s.) |
| 0.1% | −28% | n.s. = not significant

V. Inhibition of cell proliferation

Normal human epidermal keratinocytes (NHEK) are cultured under sterile conditions in keratinocyte growth medium (Gibco) in a humidified, 5% $CO_2$-containing atmosphere. Cells of the third passage are inoculated at a density of 12,000 cells/ml.

After 24 hours, the test substance is added to the medium and the number of cells is determined after a further 48 hours. The results were calculated in comparison to a control and are indicated as the percentage decrease in cell numbers.

The proliferation-inhibiting action of the above mentioned compound A was tested in comparison to simvastatin at concentrations of $10^{-6}$ to $10^{-10}$ mol/l.

The results are compiled in the following Table:

|  | $10^{-6}$ | $10^{-7}$ | $10^{-8}$ | $10^{-9}$ | $10^{-10}$ |
|---|---|---|---|---|---|
| A | −72% | −73% | −70% | −48% | −16% |
| Simvastatin | −68% | −51% | −20% | −21% | −7% |

VI. Determination of fungistatic activity

The fungistatic activity was determined by means of the serial dilution test (microtitre system). Sabouraud broth was used as the nutrient medium. The inoculum was approximately $10^4$ to $10^5$ CFU/ml (CFU=colony-forming units); the incubation time was 2 to 4 days at 26° C.

The minimum inhibitory concentration (MIC), i.e. the lowest concentration which no longer allowed visible growth, and the lowest concentration at which a decrease in growth of the test microorganism occurred in comparison with a control were determined.

The above mentioned compound I was tested. The results are shown in the following Table.

|  | MIC µg/ml | Decrease in growth µg/ml |
|---|---|---|
| Candida albicans ATCC 10231 | 128 | 64 |
| Rhodotorula rubra 49 | 128 | 32 |
| Sacc. carlsbergensis | 128 | 64 |

-continued

|  | MIC µg/ml | Decrease in growth µg/ml |
|---|---|---|
| ATCC 9080 |  |  |
| Aspergillus niger ATCC 16404 | >1024 | 128 |
| Trichophyton mentagrophytes ATCC 9129 | 512 |  |
| Penicillium notatum CBS 19746 | 128 | 64 |

The compounds A to I appeared to be non-toxic at the curative dose. For example, the compounds A, H and I showed no toxic effects in the mouse after oral administration of 100 mg/kg, once daily for 4 days.

For pharmaceutical use, the compounds of the general formula I may be incorporated into the customary pharmaceutical preparation forms for oral, rectal and topical administration in a manner known per se.

Formulations for oral administration include, for example, tablets, coated tablets and capsules, and (for rectal administration) suppositories are preferred. The daily dose is between 0.1 and 500 mg for a human of 60 kg body weight, but a daily dose of 0.5 to 100 mg for a human of 60 kg body weight is preferred. The daily dose is preferably divided into 1 to 3 individual doses.

In the case of topical use, the compounds may be administered in preparations which contain approximately 1 to 1000 mg, in particular 10 to 300 mg, of active compound per day. The daily dose is preferably divided into 1 to 3 individual doses.

Topical formulations include gels, creams, lotions, ointments, powders, aerosols and other conventional formulations for the application of medicaments to the skin. The amount of active compound for topical application is 1 to 50 mg per gram of formulation, but preferably 5 to 20 mg per gram of formulation. In addition to application to the skin, the topical formulations of the present invention may also be used in the treatment of mucous membranes which are accessible to topical treatment. For example, the topical formulations may be applied to the mucous membranes of the mouth, the lower colon, etc.

For use in poultry breeding to produce low-cholesterol eggs, the active compounds of the general formula I are administered to the animals by the customary methods as an additive to suitable foodstuffs. The concentration of the active compounds in the finished feed is normally 0.01 to 1%, but preferably 0.05 to 0.5%.

The active compounds may be added to the feed as such. In addition to the active compound and optionally in addition to a customary vitamin/mineral mixture, the foodstuffs for laying hens according to the invention may thus contain, for example, maize, soya bean flour, meat meal, feed fat and soya oil. One of the compounds of the formula I mentioned above is admixed to this feed as an active compound in a concentration of 0.01 to 1%, but preferably 0.05 to 0.5%.

The following Examples serve to illustrate the invention in greater detail. The $R_f$ values indicated were determined on ready-to-use plates from E. Merck, Darmstadt, namely:

a) Alumina F-254 (Type E)

b) Silica gel 60 F-254.

Examples for the preparation of the starting materials:

EXAMPLE A

Diethyl 4-cyanobenzylphosphonate 98 g of 4-(bromomethyl)benzonitrile and 300 ml of triethyl phosphite are heated at 140° C. until the reaction is initiated. The mixture is then reflux-heated at a bath temperature of 150°–160° C. for a further 2 hours, the ethyl bromide formed is removed by distillation, the mixture is heated at 150° C. for a further hour and triethyl phosphite is then removed by distillation in vacuo. The residue is treated with 250 ml of cyclohexane in an ice bath, and the crystals formed are suction-filtered and washed with 150 ml of cyclohexane. 125.6 g (99.2% of theory) of the title compound of melting point 41.5°–43° C. are obtained.

The following were obtained in the same manner:
a) diethyl 3-cyanobenzylphosphonate from 3-(bromomethyl)benzonitrile and triethyl phosphite. Colourless oil.
b) diethyl 4-methoxycarbonyl-3-methylbenzylphosphonate from 4-methoxycarbonyl-3-methylbenzyl bromide (J. Med. Chem. 33, 2437–2451 [1990]) and triethyl phosphite. Colourless oil.
c) diethyl 2-fluoro-4-methoxycarbonylbenzylphosphonate from 2-fluoro-4-methoxycarbonylbenzyl bromide (prepared from methyl 3-fluoro-4-methylbenzoate and bromine in the presence of benzoyl peroxide in carbon tetrachloride with exposure to a 1000 Watt tungsten lamp) and triethyl phosphite. Colourless oil.
d) diethyl 2-bromo-4-methoxycarbonylbenzylphosphonate from 2-bromo-4-methoxycarbonylbenzyl bromide (prepared from methyl 3-bromo-4-methylbenzoate and bromine in the presence of benzoyl peroxide in carbon tetrachloride with exposure to a 1000 Watt tungsten lamp) and triethyl phosphite. Colourless oil.
e) diethyl 2-methoxy-4-methoxycarbonylbenzylphosphonate from 2-methoxy-4-methylbenzyl bromide (prepared from methyl 3-methoxy-4-methylbenzoate and bromine in the presence of benzoyl peroxide in carbon tetrachloride with exposure to a 1000 Watt tungsten lamp) and triethyl phosphite. Colourless oil.

EXAMPLE B

Diethyl 1-(4-cyanophenyl)ethylphosphonate 18.7 ml of a 1.6M solution of n-butyllithium in n-hexane are added dropwise with stirring at −50° C. to a solution of 7.5 g of diethyl 4-cyanobenzylphosphonate in 60 ml of tetrahydrofuran, the mixture is subsequently stirred at −40° C. for 25 minutes and 4.7 g of methyl iodide in 20 ml of tetrahydrofuran are then added dropwise at −40° C. After stirring overnight at ambient temperature, the mixture is evaporated down, the residue is taken up in ethyl acetate and washed with water, and the organic phase is dried and evaporated down. After purification by column chromatography on Silica gel (petroleum ether/2-propanol=6:1 to 2:1, v/v), 5.7 g of the title compound are obtained as a colourless oil. $R_f$ value: 0.52 (Silica gel, petroleum ether/2-propanol= 3:1, v/v).

EXAMPLE C

N-(4-Chlorobenzoyl)-4-piperidone 87.5 g of 4-chlorobenzoyl chloride and a solution of 276 g of potassium carbonate in 552 ml of water cooled to 5° C. are added successively with stirring to a suspension of 80.6 g of powdered 4-piperidone hydrochloride hydrate in 1 l of tetrahydrofuran. The mixture is stirred at ambient temperature for a further 45 minutes. The organic phase is then separated off, the aqueous phase is extracted twice more with ethyl acetate, and the organic phases are combined, dried and evaporated down. The residue is dissolved in ethyl acetate and the solution is treated with petroleum ether. 88.6 g of the title compound of melting point 61°–63° C. are obtained.

The following were obtained analagously:
a) N-(4-chlorobenzenesulphonyl)-4-piperidone from 4-piperidone hydrochloride hydrate and 4-chlorobenzenesulphonyl chloride. Melting point: 158°–160° C.
b) N-(4-methylbenzoyl)-4-piperidone from 4-methylbenzoyl chloride and 4-piperidone hydrochloride hydrate. Colourless resin.
c) N-(4-dihydrocinnamoyl)-4-piperidone from 4-dihydrocinnamoyl chloride and 4-piperidone hydrochloride hydrate. Colourless crystals.
d) N-(4-chlorocinnamoyl)-4-piperidone from 4-chlorocinnamoyl chloride and 4-piperidone hydrochloride hydrate. Colourless resin.
e) N-hexanoyl-4-piperidone from hexanoyl chloride and 4-piperidone hydrochloride hydrate. Colourless oil.
f) N-pivaloyl-4-piperidone from pivaloyl chloride and 4-piperidone hydrochloride hydrate. Colourless crystals.
g) N-cyclohexanecarbonyl-4-piperidone from cyclohexanecarbonyl chloride and 4-piperidone hydrochloride hydrate. Colourless crystals.

EXAMPLE D 1-(4-Chlorobenzoyl)-4-(4-cyanobenzylidene)piperidine 7.6 g of diethyl 4-cyanobenzylphosphonate in 50 ml of tetrahydrofuran are added dropwise at −50° C. to a solution of lithium diisopropylamide prepared from 3.34 g of diisopropylamine in 20 ml of tetrahydrofuran and 19 ml of a 1.6M solution of n-butyllithium in n-hexane. After stirring for 20 minutes at this temperature, a solution of 7.13 g of N-(4-chlorobenzoyl)-4-piperidone is added dropwise. The mixture is allowed to warm to ambient temperature, is poured onto ice after a further 2 hours and is extracted with ethyl acetate. The organic phase is dried and evaporated down. After recrystallization from ethyl acetate, 7.6 g of the title compound of melting point 134°–135.5° C. are obtained.

The following were obtained analogously:
a) 1-(4-chlorobenzoyl)-4-(3-cyanobenzylidene)piperidine from diethyl 3-cyanobenzylphosphonate and N-(4-chlorobenzoyl)- 4-piperidone. Colourless foam.
b) 1-(4-chlorobenzenesulphonyl)-4-(4-cyanobenzylidene)piperidine from diethyl 4-cyanobenzylphosphonate and N-(4-chlorobenzenesulphonyl)- 4-piperidone. Melting point: 129°–130° C.
c) 1-(4-chlorobenzoyl)-4-(4-cyano-α-methylbenzylidene)piperidine from diethyl 1-(4-cyanophenyl)ethylphosphonate and N-(4-chlorobenzoyl)- 4-piperidone. Melting point: 134° C.
d) 1-benzyl-3-(4-cyanobenzylidene)piperidine from diethyl-4-cyanobenzylphosphonate and N-benzyl-3-piperidone. Melting point: 113° C.
e) 1-(4-chlorobenzoyl)-4-(4-methoxycarbonyl-3-methylbenzylidene)piperidine from diethyl 4-methoxycarbonyl-3-methylbenzylphosphonate and N-(4-chlorobenzoyl)-4-piperidone. Melting point: 142°–144° C.
f) 1-(4-chlorobenzoyl)-4-(2-fluoro-4-methoxycarbonylbenzylidene)piperidine from diethyl 2-fluoro-4-methoxycarbonylbenzylphosphonate and N-(4-chlorobenzoyl)-4-piperidone. Melting point: 110°–112° C.
g) 4-(2-bromo-4-methoxycarbonylbenzylidene)-1-(4-chlorobenzoyl)piperidine from diethyl 2-bromo-4-methoxycarbonylbenzylphosphonate and N-(4-chlorobenzoyl)-4-piperidone. Melting point: 140°–142° C.

h) 1-(4-chlorobenzoyl)-4-(2-methoxy-4-methoxycarbonylbenzylidene)piperidine from diethyl 2-methoxy-4-methoxycarbonylbenzylphosphonate and N-(4-chlorobenzoyl)-4-piperidone. Colorless oil.

EXAMPLE E 1-(4-Chlorobenzoyl)-3-(4-cyanobenzylidene)piperidine 1.8 g of 1-chloroethyl chloroformate in 5 ml of methylene chloride are added dropwise to 2.9 g of 1-benzyl- 3-(4-cyanobenzylidene)piperidine in 20 ml of methylene chloride at 0° C. and the mixture is stirred at 0° C. for 30 minutes. After 20 minutes at ambient temperature, it is evaporated down, the residue is taken up in 20 ml of methanol and the mixture is reflux-heated for 30 minutes. The reaction solution is evaporated down, and the residue is triturated with 100 ml of ethyl acetate and suction-filtered. 1.9 g of 3-(4-cyanobenzylidene)piperidine hydrochloride are obtained as a colourless powder.

This product and 2.1 g of triethylamine are dissolved in 15 ml of methylene chloride and 1.75 g of 4-chlorobenzoyl chloride in 5 ml of methylene chloride are added dropwise at ambient temperature. After 30 minutes at ambient temperature, 100 ml of methylene chloride are added, the mixture is extracted twice by shaking with water, the extracts are dried using anhydrous magnesium sulphate and evaporated down, and the residue is purified by column chromatography (Silica gel, ethyl acetate). 1.8 g of the title compound are obtained as colourless crystals of melting point >210° C.

EXAMPLE F 1-(4-Chlorobenzoyl)-4-(4-cyanobenzyl)piperidine 8.4 g of 1-(4-chlorobenzoyl)-4-(4-cyanobenzylidene)piperidine are hydrogenated (5 bar) at ambient temperature for 15 minutes in 400 ml of toluene with the addition of 2 g of palladium black. After addition of 1 g of palladium black, the mixture is hydrogenated for an additional 2.5 hours, a further 1 g of catalyst is added and the mixture is hydrogenated for an additional hour. 7.9 g (93.3% of theory) of the title compound are obtained as a colourless powder of melting point 137°–139° C.

EXAMPLE G 1-(4-Chlorobenzoyl)-4-(4-ethoxyimidoylbenzylidene)piperidine hydrochloride 40.7 g of hydrogen chloride are introduced with ice-cooling into a suspension of 10.8 g of 1-(4-chlorobenzoyl)-4-(4-cyanobenzylidene)piperidine in 70 ml of anhydrous ethanol. After stirring for 16 hours at ambient temperature, the solvent is evaporated at a bath temperature of 30° C., the residue is dissolved again in 35 ml of ethanol and the solution is then evaporated down again. The residue is triturated with ethyl acetate. 13.2 g of the title compound are obtained as a colourless powder.

The following were obtained analogously:
a) 1-(4-chlorobenzoyl)-4-(3-methoxyimidoylbenzylidene)piperidine hydrochloride from 1-(4-chlorobenzoyl)-4-(3-cyanobenzylidene)piperidine and methanol. Colourless resin.
b) 1-(4-Chlorobenzenesulphonyl)-4-(4-methoxyimidoylbenzylidene)piperidine hydrochloride from 1-(4-chlorobenzenesulphonyl)-4-(4-cyanobenzylidene)piperidine and methanol. Colourless resin.
c) 1-(4-chlorobenzoyl)-4-(4-ethoxyimidoyl-α-methylbenzylidene)piperidine hydrochloride from 1-(4-chlorobenzoyl)-4-(4-cyano-α-methylbenzylidene)piperidine and ethanol. Colourless foam.
d) 1-(4-chlorobenzoyl)-3-(4-ethoxyimidoylbenzylidene)piperidine hydrochloride from 1-(4-chlorobenzoyl)-3-(4-cyanobenzylidene)piperidine. Colourless crystals.
e) 1-(4-chlorobenzoyl)-4-(4-ethoxyimidoylbenzyl)piperidine hydrochloride from 1-(4-chlorobenzoyl)-4-(4-cyanobenzyl)piperidine. Melting point: 236° C.

EXAMPLE H

Diethyl 4-ethoxyimidoylbenzylphosphonate hydrochloride 5.6 g of diethyl 4-cyanobenzylphosphonate and 24 g of hydrogen chloride in 35 ml of anhydrous ethanol are stirred at ambient temperature for 17 hours. The reaction solution is then evaporated down and the residue is in each case evaporated to dryness twice more after addition of ethanol. The colourless crystals obtained are reacted further without purification.

EXAMPLE I

Diethyl 4-(2-oxazolin-2-yl)benzylphosphonate

The product obtained in Example H is dissolved in 50 ml of ethanol. After the addition of 1.8 g of ethanolamine and 4.1 g of triethylamine, the reaction solution is reflux-heated for 2 hours and then evaporated down at 50° C., and the residue is dissolved in 100 ml of ethyl acetate. The solution is washed three times with water, dried and evaporated down. 4.2 g of the title compound of melting point 65° C. are obtained.

EXAMPLE K

4-[4-(2-Oxazolin-2-yl)benzylidene]-1-tritylpiperidine 6.25 ml of a 1.6M solution of n-butyllithium in hexane followed, after stirring for 20 minutes, by 3.4 g of N-trityl-4-piperidone (prepared from 4-piperidone hydrochloride hydrate and trityl chloride) in 20 ml of tetrahydrofuran are added dropwise at −60° C. to 2.97 g of diethyl 4-(2-oxazolin-2-yl)benzylphosphonate. The mixture is stirred at −60° C. for 25 minutes. The reaction solution is then allowed to warm to ambient temperature and is stirred for a further 1.5 hours at this temperature. The reaction solution is then stirred into 150 ml of ice-water, the mixture is extracted three times with 150 ml of ethyl acetate, and the organic phase is dried and evaporated down. The residue is purified by column chromatography on Silica gel (petroleum ether/ethyl acetate=1:1, v/v). 1.7 g of the title compound of melting point 110°–115° C. are obtained.

The following were prepared analogously:
a) 4-[4-(2-oxazolin-2-yl) benzylidene]-1-tritylhexahydroazepine from diethyl 4-(2-oxazolin-2-yl)benzylphosphonate and 1-tritylhexahydroazepin- 4-one (prepared from hexahydroazepin- 4-one and trityl chloride). Colourless foam. $R_f$ value: 0.40 (Silica gel: petroleum ether/ethyl acetate=1:1, v/v).
b) 1-tert.butoxycarbonyl-4-[4-(2-oxazolin-2-yl)benzylidene] piperidine from diethyl 4-(2-oxazolin-2-yl)benzylphosphonate and N-tert.butoxycarbonyl- 4-piperidone (prepared from 4-piperidone hydrochloride hydrate and di-tert.butyl pyrocarbonate. Melting point: 74° C.

EXAMPLE L 1-tert.Butoxycarbonyl-
4-[4-(2-oxazolin-2-yl)benzyl)piperidine 2.4 g (7 mmool) of 1-tert.butoxycarbonyl-4-[4-(2-oxazolin- 2-yl)benzylidene]piperidine, dissolved in 70 ml of anhydrous ethanol and 20 ml of ethyl acetate, are catalytically hydrogenated (ambient temperature, 20 minutes, hydrogen pressure 50 psi) in the presence of 2.5 g of palladium-carbon (10%). The catalyst is suction-filtered, the filtrate is evaporated down and the residue is reacted further without purification.

EXAMPLE M

4-[4-(2-Oxazolin-2-yl)benzylidene]piperidine 1.0 g of 4-[4-(2-oxazolin-2-yl) benzylidene]-1-tritylpiperidine in 20 ml of methylene chloride are treated slowly with 2 ml of trifluoroacetic acid at −10° C. After stirring for 1 hour at −10° C., the reaction mixture is poured into 150 ml of ice-water and immediately adjusted to pH 11.5 using 6N sodium hydroxide solution. After stirring for 10 minutes, it is extracted twice with 150 ml of ether, and the combined organic phases are washed, dried and evaporated down. The residue is purified by column chromatography on alumina (methylene chloride/methanol=40:1, v/v). 340 mg of the title compound of melting point 126° C. are obtained.

The following were obtained analogously:
a) 4-[4-(2-oxazolin-2-yl) benzylidene]hexahydroazepine from 4-[4-(2-oxazolin-2-yl)benzylidene]-1-tritylhexahydroazepine and trifluoroacetic acid. Melting point: sinters from 46° C.
b) 4-[4-(2-oxazolin-2-yl)benzyl]piperidine from 1-tert.butoxycarbonyl-4-[4-(2-oxazolin-2-yl)benzyl] piperidine and trifluoroacetic acid. Melting point: 110° C.

EXAMPLE N

3-[4-(2-Oxazolin-2-yl)benzylidene]pyrrolidine

A solution of 5.0 g of N-acetyl-2-pyrrolidone and 5.17 g of 4-cyanobenzaldehyde in 50 ml of tetrahydrofuran is added dropwise to a suspension of 5.36 g of sodium hydride (55% in oil) in 50 ml of tetrahydrofuran at 5°–10° C. and the mixture is then stirred at 0° C. for 1 hour. Excess sodium hydride is eliminated by the addition of some methanol, and the reaction mixture is poured onto ice and neutralized with glacial acetic acid. The precipitate is suction-filtered and dissolved in a methylene chloride/methanol mixture, and the solution is dried and evaporated down. The residue is triturated with ether and suction-filtered. 1.4 g of 3-(4-cyanobenzylidene)- 2-pyrrolidone are obtained as a colourless powder of melting point 260° C.

1.36 g of this product are suspended in 30 ml of methanol. About 10 g of hydrogen chloride are introduced, with ice-cooling, then the mixture is stirred at ambient temperature for 20 hours and allowed to stand at ambient temperature for 2 days. After evaporating down, the residue is taken up in 40 ml of ethanol, 0.68 g of ethanolamine and 1.52 g of triethylamine are added, and the mixture is reflux-heated for 2 hours and then evaporated down. The residue is triturated with a water/ethyl acetate mixture and the precipitate is then suction-filtered and dried. 1.5 g of 3-[4-(2-oxazolin-2-yl)benzylidene]-2-pyrrolidone of melting point 258°–262° C. are obtained.

152 mg of lithium aluminium hydride are added to 0.49 g of this product in 10 ml of tetrahydrofuran and the mixture is stirred at ambient temperature for 2 hours. After the addition of 0.3 ml of water, the mixture is stirred at ambient temperature for half an hour and the precipitate is then suction-filtered. The title compound obtained is reacted further as a solution.

EXAMPLE O 1-(4-Chlorobenzoyl)-4-[2-
fluoro-4-(2-hydroxyethylaminocarbonyl)benzylidene]
piperidine 9.0 g of 1-(4-chlorobenzoyl)-4-[2-fluoro-4-methoxycarbonylbenzylidene] piperidine in 150 ml of methanol are treated with a solution of 4.0 g of 84% caustic potash in 100 ml of water and the mixture is stirred overnight at ambient temperature. The methanol is evaporated off, the residue is mixed water with cooling and the mixture is acidified with dilute hydrochloric acid. The precipitate is suction-filtered, washed with water and dried in vacuo. 8.6 g (95% of theory) of 4-(4-carboxy- 2-fluorobenzylidene)-1-(4-chlorobenzoyl)piperidine of melting point 170°–173° C. are obtained.

2.0 g of this product and 0.88 g of N,N'-carbonyldiimidazole in 50 ml of xylene are heated at 60° C. for 1 hour, then 0.32 g of ethanolamine are added and the mixture is stirred at a bath temperature of 160° C. for 3 hours. After evaporation of the solvent, the residue is mixed with water, extracted three times with methylene chloride, and the organic extract is dried and evaporated down. The residue is purified by column chromatography (Silica gel: ethyl acetate/methanol=10:0.5, v/v). 0.4 g of the title compound is obtained as a colourless oil. $R_f$ value: 0.25 (Silica gel: ethyl acetate/methanol=10:0.5, v/v).

The following were prepared analogously:
a) 1-(4-Chlorobenzoyl)-4-[4-(2-hydroxyethylaminocarbonyl)- 3-methylbenzylidene]piperidine from 1-(4-chlorobenzoyl)-4-(4-methoxycarbonyl-3-methylbenzylidene)piperidine and ethanolamine. Colourless oil. $R_f$ value: 0.2 (Silica gel: ethyl acetate/petroleum ether/methanol= 10:5:1, v/v/v).

The hydrolysis of the starting ester was carried out at boiling temperature.
b) 4-[2-bromo-4-(2-hydroxyethylaminocarbonyl)benzylidene]- 1-(4-chlorobenzoyl)piperidine from 4-(2-bromo-4-methoxycarbonylbenzylidene)-1-(4-chlorobenzoyl)piperidine and ethanolamine. Melting Point: 90°–92° C.
c) 1-(4-chlorobenzoyl)-4-[4-(2-hydroxyethylaminocarbonyl)- 2-methoxybenzylidene]piperidine from 4-(2-methoxy-4-methoxycarbonylbenzylidene)-1-(4-chlorobenzoyl)piperidine and ethanolamine. Colorless oil.
Examples for the preparation of the final products:

EXAMPLE 1

1-(4-Chlorobenzoyl)-4-[4-(2-oxazolin-2-
yl)benzylidene]piperidine 13.2 g (0.0315 mol) of 1-(4-chlorobenzoyl)-4-(4-ethoxyimidoylbenzylidene)piperidine hydrochloride are suspended in 59 ml of anhydrous ethanol. After the addition of 2.64 g (0.042 mol) of ethanolamine and 6.5 g (0.063 mol) of triethylamine, the mixture is reflux-heated for 1.5 hours.

After cooling in an ice-bath, the precipitate is suction-filtered and washed with ethanol. 10.4 g (88.6% of theory) of the title compound of melting point 181°–183° C. are obtained.

$^1$H-NMR spectrum (200 MHz, CDCl$_3$); signals at ppm: 2.3–2.6 (m,4H), 3.3–3.9 (m,4H), 4.05 (t,2H), 4.4 (t,2H), 6.4 (s,1H), 7.2 (d,2H), 7.4 (s,4H), 7.9 (d,2H).

The hydrochloride of the title compound was prepared in the cold in ethanol using ethereal hydrochloric acid. It sinters at 69°–71° C. and becomes solid again at 80°–81° C. with evolution of gas.

The following were obtained analogously:

a) 1-(4-chlorobenzenesulphonyl)-4-[4-(2-oxazolin-2-yl)benzylidene] piperidine from 1-(4-chlorobenzenesulphonyl)-4-(4-methoxyimidoylbenzylidene)piperidine hydrochloride and ethanolamine. Melting point: 191.5°–192.5° C.

b) 1-(4-Chlorobenzoyl)-4-[4-(4,5-dihydro-6H-oxazin-2-yl)benzylidene] piperidine from 1-(4-chlorobenzoyl)-4-(4-ethoxyimidoyl-benzylidene)piperidine hydrochloride and 3-aminopropanol. Melting point: 159°–160° C.

c) 1-(4-chlorobenzoyl)-4-[4-(4,4-dimethyl-2-oxazolin-2-yl)-benzylidene] piperidine from 1-(4-chlorobenzoyl)-4-(4-ethoxyimidoylbenzylidene)piperidine hydrochloride and 2-amino-2-methylpropanol. Melting point: 145°–146° C.

d) 1-(4-chlorobenzoyl)-4-[4-(2-thiazolin-2-yl)benzylidene] piperidine from 1-(4-chlorobenzoyl)-4-(4-ethoxyimidoylbenzylidene)piperidine hydrochloride and cysteamine. Melting point: 162°–163° C.

e) 1-(4-chlorobenzoyl)-4-[4-(R-5-methyl-2-oxazolin-2-yl)benzylidene] piperidine from 1-(4-chlorobenzoyl)-4-(4-ethoxyimidoylbenzylidene)piperidine hydrochloride and R-1-amino-2-propanol. Melting point: 104°–106° C.

f) 1-(4-chlorobenzoyl)-4-[4-(S-5-methyl-2-oxazolin-2-yl)-benzylidene] piperidine from 1-(4-chlorobenzoyl)-4-(4-ethoxyimidoylbenzylidene)piperidine hydrochloride and S-1-amino-2-propanol. Melting point: 107°–108° C.

g) 1-(4-chlorobenzoyl)-4-[3-(2-oxazolin-2-yl)benzylidene] piperidine from 1-(4-chlorobenzoyl)-4-(3-methoxyimidoylbenzylidene)piperidine hydrochloride and ethanolamine. Melting point: 90°–92° C.

h) 1-(4-chlorobenzoyl)-4-[4-(5,5-dimethyl-2-oxazolin-2-yl)benzylidene] piperidine from 1-(4-chlorobenzoyl)-4-(4-ethoxyimidoylbenzylidene)piperidine hydrochloride and 2-hydroxy-2-methylpropylamine. Melting point: 145°–146° C.

i) 1-(4-chlorobenzenesulphonyl)-4-[4-(2-imidazolin-2-yl)benzylidene] piperidine from 1-(4-chlorobenzenesulphonyl)-4-(4-methoxyimidoylbenzylidene)piperidine hydrochloride and ethylenediamine. Melting point: 222°–224° C.

j) 1-(4-chlorobenzenesulphonyl)-4-[4-(N-methyl-2-imidazolin-2-yl)benzylidene]piperidine from 1-(4-chlorobenzenesulphonyl)-4-(4-methoxyimidoylbenzylidene)piperidine hydrochloride and N-methylethylenediamine. Colourless foam. R$_f$ value: 0.24 (alumina; ethyl acetate).

k) 1-(4-chlorobenzoyl)-4-[4-(S-4-methyl-2-oxazolin-2-yl)benzylidene] piperidine from 1-(4-chlorobenzoyl)-4-(4-ethoxyimidoylbenzylidene)piperidine hydrochloride and L-alaninol. Melting point: 143° C.

l) 1-(4-chlorobenzoyl)-4-[4-(R-4-methyl-2-oxazolin-2-yl)benzylidene] piperidine from 1-(4-chlorobenzoyl)-4-(4-ethoxyimidoylbenzylidene)piperidine hydrochloride and D-alaninol. Melting point: 143° C.

m) 1-(4-chlorobenzoyl)-4-[4-(5-phenyl-2-oxazolin-2-yl)benzylidene] piperidine from 1-(4-chlorobenzoyl)-4-(4-ethoxyimidoylbenzylidene)piperidine hydrochloride and 2-amino-1-phenylethanol. Melting point: 147° C.

n) 1-(4-chlorobenzoyl)-4-[4-(5-diethylaminomethyl-2-oxazolin-2-yl)benzylidene]piperidine from 1-(4-chlorobenzoyl)-4-(4-ethoxyimidoylbenzylidene)piperidine hydrochloride and 1-amino-3-diethylamino-2-propanol. Melting point: 91° C.

o) 1-(4-chlorobenzoyl)-4-[4-(4-hydroxymethyl-2-oxazolin-2-yl)benzylidene]piperidine from 1-(4-chlorobenzoyl)-4-(4-ethoxyimidoylbenzylidene)piperidine hydrochloride and DL-serinol. Melting point: 137° C.

p) 1-(4-chlorobenzoyl)-4-[4-(2-oxazolin-2-yl)-α-methylbenzylidene]piperidine from 1-(4-chlorobenzoyl)-4-(4-ethoxyimidoyl-α-methylbenzylidene)piperidine hydrochloride and ethanolamine. Melting point: 192° C.

q) 1-(4-chlorobenzoyl)-4-[4-(R-4-phenyl-2-oxazolin-2-yl)benzylidene] piperidine from 1-(4-chlorobenzoyl)-4-(4-ethoxyimidoylbenzylidene)piperidine and R-2-amino-2-phenylethanol. Melting point: 130° C.

r) 4-[4-(R-4-benzyl-2-oxazolin-2-yl)benzylidene]-1-(4-chlorobenzoyl)piperidine from 1-(4-chlorobenzoyl)-4-(4-ethoxyimidoylbenzylidene)piperidine and R-2-amino-3-phenyl-1-propanol. Melting point: 142° C.

s) 4-[4-(S-4-benzyl-2-oxazolin-2-yl)benzylidene]-1-(4-chlorobenzoyl)piperidine from 1-(4-chlorobenzoyl)-4-(4-ethoxyimidoylbenzylidene)piperidine and S-2-amino-3-phenyl-1-propanol. Melting point: 142°–143° C.

t) 1-(4-chlorobenzoyl)-4-[4-(4-((4-chlorobenzyl))-2-oxazolin- 2-yl)benzylidene]piperidine from 1-(4-chlorobenzoyl)-4-(4-ethoxyimidoylbenzylidene)piperidine and 4-chlorophenylalaninol. Melting point: 127° C.

u) 1-(4-chlorobenzoyl)-4-[4-(4-((2-methylthioethyl))-2-oxazolin- 2-yl)benzylidene]piperidine from 1-(4-chlorobenzoyl)-4-(4-ethoxyimidoylbenzylidene)piperidine and L-methioninol. Melting point: 95°–96° C.

v) 1-(4-chlorobenzoyl)-4-[4-(4-((1-methyl-S-propyl))-2-oxazolin- 2-yl)benzylidene]piperidine from 1-(4-chlorobenzoyl)-4-(4-ethoxyimidoylbenzylidene)piperidine and S-isoleucinol. Melting point: 101° C.

w) 1-(4-chlorobenzoyl)-4-[4-(2-imidazolin-2-yl)benzyl] piperidine from 1-(4-chlorobenzoyl)-4-(4-ethoxyimidoylbenzyl)piperidine hydrochloride and ethylenediamine. Melting point: 155°–157° C.

x) 1-(4-chlorobenzoyl)-4-[4-(S-4-methyl-2-oxazolin-2-yl)benzyl] piperidine from 1-(4-chlorobenzoyl)-4-(4-ethoxyimidoylbenzyl)piperidine hydrochloride and L-alaninol. Melting point: 92°–95° C.

y) 1-(4-chlorobenzoyl)-4-[4-(N-methyl-2-imidazolin-2-yl)benzyl] piperidine from 1-(4-chlorobenzoyl)-4-(4-ethoxyimidoylbenzyl)piperidine hydrochloride and N-methylethylenediamine. Melting point: 163°–167° C.

z) 1-(4-chlorobenzoyl)-4-[4-(S-5-methyl-2-oxazolin-2-yl)benzyl] piperidine from 1-(4-chlorobenzoyl)-4-(4-ethoxyimidoylbenzyl)piperidine hydrochloride and S-1-amino-2-propanol. Melting point: 98°–100° C.

aa) 1-(4-chlorobenzoyl)-4-[4-(R-5-methyl-2-oxazolin-2-yl)benzyl] piperidine from 1-(4-chlorobenzoyl)-4-(4-ethoxyimidoylbenzyl)piperidine hydrochloride and R-1-amino-2-propanol. Melting point: 99°–101° C.

ab) 1-(4-chlorobenzoyl)-4-[4-(2-thiazolin-2-yl)benzyl]piperidine from 1-(4-chlorobenzoyl)-4-(4-ethoxyimidoylbenzyl)piperidine hydrochloride and cysteamine. Melting point: 106°–108° C.

ac) 1-(4-chlorobenzoyl)-4-[4-(4,5-dihydro-6H-oxazin-2-yl)benzyl] piperidine from 1-(4-chlorobenzoyl)-4-(4-ethoxyimidoylbenzyl)piperidine hydrochloride and 3-aminopropanol. Melting point: 106°–108° C.

ad) 1-(4-chlorobenzoyl)-3-[4-(2-oxazolin-2-yl)benzylidene] piperidine from 1-(4-chlorobenzoyl)-3-(4-ethoxyimidoylbenzylidene)piperidine hydrochloride and ethanolamine. Melting point: 151° C.

EXAMPLE 2

1-(4-Chlorobenzoyl)-4-[4-(2-oxazolin-2-yl)benzylidene]piperidine 12.5 ml (0.021 mol) of a 1.6M solution of n-butyllithium in n-hexane are added dropwise at −50° C. to 6 g (0.02 mol) of diethyl 4-(2-oxazolin-2-yl)benzylphosphonate in 80 ml of tetrahydrofuran. The deep-red solution is stirred at −55° C. for 25 minutes and 4.7 g (0.02 mol) of N-(4-chlorobenzoyl)-4-piperidone in 20 ml of tetrahydrofuran are then added dropwise. After stirring for 5 hours at ambient temperature, the reaction mixture is stirred into 300 ml of water, and the precipitate is suction-filtered after a further 20 minutes and recrystallized from ethanol. 3.2 g (42% of theory) of the title compound identical to the product mentioned in Example 1 are obtained.

The following were obtained analogously:
a) 1-(4-methylbenzoyl)-4-[4-(2-oxazolin-2-yl)benzylidene] piperidine from diethyl 4-(2-oxazolin-2-yl)benzylphosphonate and N-(4-methylbenzoyl)-4-piperidone. Melting point: 169°–171° C.
b) 1-(dihydrocinnamoyl)-4-[4-(2-oxazolin-2-yl)benzylidene] piperidine from diethyl 4-(2-oxazolin-2-yl)benzylphosphonate and N-dihydrocinnamoyl-4-piperidone. Melting point: 98°–100° C.
c) 1-(4-chlorocinnamoyl)-4-[4-(2-oxazolin-2-yl)benzylidene] piperidine from diethyl 4-(2-oxazolin-2-yl)benzylphosphonate and N-(4-chlorocinnamoyl)-4-piperidone. $R_f$ value: 0.86 (alumina; ethyl acetate)
d) 1-hexanoyl-4-[4-(2-oxazolin-2-yl)benzylidene]piperidine from diethyl 4-(2-oxazolin-2-yl)benzylphosphonate and N-hexanoyl-4-piperidone. Melting point: 98°–100° C.
e) 4-[4-(2-oxazolin-2-yl)benzylidene]-1-pivaloylpiperidine from diethyl 4-(2-oxazolin-2-yl)benzylphosphonate and N-pivaloyl-4-piperidone. Melting point: 163°–165° C.
f) 1-cyclohexanecarbonyl-4-[4-(2-oxazolin-2-yl)benzylidene] piperidine from diethyl 4-(2-oxazolin-2-yl)benzylphosphonate and N-cyclohexanecarbonyl-4-piperidone. Melting point: 163°–164° C.

EXAMPLE 3

4-[4-(2-Oxazolin-2-yl)benzylidene]-1-(4-trifluoromethylbenzoyl)piperidine 120 mg (0.5 mmol) of 4-[4-(2-oxazolin-2-yl)benzylidene] piperidine and 75 mg (0.75 mmol) of triethylamine in 3 ml of ethyl acetate and 2 ml of methylene chloride are cooled to −5° to −10° C. and 104.3 mg (0.5 mmol) of 4-trifluoromethylbenzoyl chloride are added. The mixture is stirred at ambient temperature for 1.5 hours, diluted with ethyl acetate, washed successively with water, 2N sodium hydroxide solution and saturated saline solution, dried and evaporated down. 115 mg (56% of theory) of the title compound of melting point 142° C. are obtained.

$^1$H-NMR spectrum (200 MHz, $CDCl_3$); signals at ppm: 2.3–2.7 (m,4H), 3.3–3.5 (m,2H), 3.7–3.9 (m,2H), 4.05 (t,3H), 4.4 (t,3H), 6.4 (s,1H), 7.2 (d,2H) 7.55 (d,2H), 7.7 (d,2H), 7.9 (d,2H).

The following were obtained analogously:
a) 4-[4-(2-oxazolin-2-yl)benzylidene]-1-stearoylpiperidine from 4-[4-(2-oxazolin-2-yl)benzylidene]piperidine and stearoyl chloride. Melting point: 72° C.
b) 1-cyclopropylcarbonyl-4-[4-(2-oxazolin-2-yl)benzylidene] piperidine from 4-[4-(2-oxazolin-2-yl)benzylidene]piperidine and cyclopropanecarbonyl chloride. Melting point: 117° C.
c) 1-(4-chloro-3-methylbenzoyl)-4-[4-(2-oxazolin-2-yl)benzylidene] piperidine from 4-[4-(2-oxazolin-2-yl)benzylidene]piperidine and 4-chloro-3-methylbenzoyl chloride. Melting point: 145° C.
d) 1-(3,4-dichlorophenylacetyl)-4-[4-(2-oxazolin-2-yl)benzylidene] piperidine from 4-[4-(2-oxazolin-2-yl)benzylidene]piperidine and 3,4-dichlorophenylacetyl chloride. Melting point: 132° C.
e) 1-(4-fluorobenzoyl)-4-[4-(2-oxazolin-2-yl)benzylidene] piperidine from 4-[4-(2-oxazolin-2-yl)benzylidene]piperidine and 4-fluorobenzoyl chloride. Melting point: 146° C.
f) 1-(5-chloro-2-thienoyl)-4-[4-(2-oxazolin-2-yl)benzylidene] piperidine from 4-[4-(2-oxazolin-2-yl)benzylidene]piperidine and 5-chlorothiophenecarbonyl chloride. Melting point: 145° C.
g) 1-(2-naphthylacetyl)-4-[4-(2-oxazolin-2-yl)benzylidene] piperidine from 4-[4-(2-oxazolin-2-yl)benzylidene]piperidine and 2-naphthaleneacetyl chloride Melting point: 133° C.
h) 1-(4-chlorobenzoyl)-4-[4-(2-oxazolin-2-yl)benzylidene] hexahydroazepine from 4-[4-(2-oxazolin-2-yl)benzylidene]hexahydroazepine and 4-chlorobenzoyl chloride Viscous oil. $R_f$ value: 0.42 (alumina; petroleum ether/ethyl acetate= 1:1, v/v).
i) 1-(4-chlorobenzoyl)-4-[4-(2-oxazolin-2-yl)benzyl]piperidine from 4-[4-(2-oxazolin-2-yl)benzyl]piperidine and 4-chlorobenzoyl chloride. Melting point: 140° C.
j) 1-(1-naphthylcarbonyl)-4-[4-(2-oxazolin-2-yl)benzylidene] piperidine from 4-[4-(2-oxazolin-2-yl)benzylidene]piperidine and 1-naphthalenecarbonyl chloride. Melting point: 146°–149° C.
k) 1-(3,4-difluorobenzoyl)-4-[4-(2-oxazolin-2-yl)benzylidene] piperidine from 4-[4-(2-oxazolin-2-yl)benzylidene]piperidine and 3,4-difluorobenzoyl chloride. Melting point: 133°–135° C.
l) 1-(3,5-bis-trifluoromethylbenzoyl)-4-[4-(2-oxazolin-2-yl)benzylidene]piperidine from 4-[4-(2-oxazolin-2-yl)benzylidene]piperidine and 3,5-bis-trifluoromethylbenzoyl chloride. Melting point: 137° C.
m) 1-(4-cyanobenzoyl)-4-[4-(2-oxazolin-2-yl)benzylidene] piperidine from 4-[4-(2-oxazolin-2-yl)benzylidene]piperidine and 4-cyanobenzoyl chloride. Melting point: 166° C.
n) 1-(2-naphthylcarbonyl)-4-[4-(2-Oxazolin-2-yl)benzylidene] piperidine from 4-[4-(2-oxazolin-2-yl)benzylidene]piperidine and 2-naphthalenecarbonyl chloride. Melting point: 167° C.
o) 4-[4-(2-oxazolin-2-yl)benzylidene]-1-(2-trifluoromethylbenzoyl)piperidine from 4-[4-(2-oxazolin-2-yl)benzylidene]piperidine and 2-trifluoromethylbenzoyl chloride. Melting point: 128° C.
p) 1-(3,4-dichlorobenzoyl)-4-[4-(2-oxazolin-2-yl)benzylidene] piperidine from 4-[4-(2-oxazolin-2-yl)benzylidene]piperidine and 3,4-dichlorobenzoyl chloride Melting point: 159° C.
q) 1-(4-fluoro-1-naphthylcarbonyl)-4-[4-(2-oxazolin-2-yl)benzylidene] piperidine from 4-[4-(2-oxazolin-2-yl)benzylidene]piperidine and 4-fluoronaphthalenecarbonyl chloride. Melting point: First at 132° C., then after intermediate solidification at 157° C.

r) 4-[4-(2-oxazolin-2-yl)benzylidene]-1-(pentafluorobenzoyl)piperidine from 4-[4-(2-oxazolin-2-yl)benzylidene]piperidine and pentafluorobenzoyl chloride. Melting point: 212° C.

s) 1-benzoyl-4-[4-(oxazolin-2-yl)benzylidene]piperidine from 4-[4-(2-oxazolin-2-yl)benzylidene]piperidine and benzoyl chloride. Melting point: 136° C.

t) 1-(4-methylsulphonylbenzoyl)-4-[4-(2-oxazolin-2-yl)benzylidene] piperidine from 4-[4-(2-oxazolin-2-yl)benzylidene]piperidine and 4-methylsulphonylbenzoyl chloride. Melting point: 191° C.

u) 1-(4-tert.butylbenzoyl)-4-[4-(2-oxazolin-2-yl)benzylidene] piperidine from 4-[4-(2-oxazolin-2-yl)benzylidene]piperidine and 4-tert.butylbenzoyl chloride. Melting point: 193° C.

v) 4-[4-(2-oxazolin-2-yl) benzylidene]-1-(3-trifluoromethylbenzoyl)piperidine from 4-[4-(2-oxazolin-2-yl)benzylidene]piperidine and 3-trifluoromethylbenzoyl chloride. Melting point: 99° C.

w) 1-(3-chlorobenzoyl)-4-[4-(2-oxazolin-2-yl)benzylidene] piperidine from 4-[4-(2-oxazolin-2-yl)benzylidene]piperidine and 3-chlorobenzoyl chloride Melting point: 116° C.

x) 1-(4-methoxybenzoyl)-4-[4-(2-oxazolin-2-yl)benzylidene] piperidine from 4-[4-(2-oxazolin-2-yl)benzylidene]piperidine and 4-methoxybenzoyl chloride. Melting point: 153° C.

y) 1-(2,5-difluorobenzoyl)-4-[4-(2-oxazolin-2-yl)benzylidene] piperidine from 4-[4-(2-oxazolin-2-yl)benzylidene]piperidine and 2,5-difluorobenzoyl chloride. Melting point: 137° C.

z) 1-(4-bromobenzoyl)-4-[4-(2-oxazolin-2-yl)benzylidene] piperidine from 4-[4-(2-oxazolin-2-yl)benzylidene]piperidine and 4-bromobenzoyl chloride. Melting point: 199° C.

aa) 4-[4-(2-oxazolin-2-yl)benzylidene]-1-(1,2,3,4-tetrahydro- 2-naphthylcarbonyl)piperidine from 4-[4-(2-oxazolin-2-yl)benzylidene]piperidine and 1,2,3,4-tetrahydro-2-naphthalenecarbonyl chloride. Melting point: 151° C.

ab) 1-(4-nitrobenzoyl)-4-[4-(2-oxazolin-2-yl)benzylidene] piperidine from 4-[4-(2-oxazolin-2-yl)benzylidene]piperidine and 4-nitrobenzoyl chloride. Melting point: 192° C.

ac) 1-(4-chlorophenylacetyl)-4-[4-(2-oxazolin-2-yl)benzylidene] piperidine from 4-[4-(2-oxazolin-2-yl)benzylidene]piperidine and 4-chlorophenylacetyl chloride. Melting point: 107° C.

ad) 1-benzoyl-4-[4-(2-oxazolin-2-yl)benzyl]piperidine from 4-[4-(2-oxazolin-2-yl)benzyl]piperidine and benzoyl chloride. Melting point: 78°–80° C.

ae) 1-(2-chlorobenzoyl)-4-[4-(2-oxazolin-2-yl)benzyl]piperidine from 4-[4-(2-oxazolin-2-yl)benzyl]piperidine and 2-chlorobenzoyl chloride. Melting point: 105°–108° C.

af) 1-(3-chlorobenzoyl)-4-[4-(2-oxazolin-2-yl)benzyl]piperidine from 4-[4-(2-oxazolin-2-yl)benzyl]piperidine and 3-chlorobenzoyl chloride. Resin. $R_f$ value: 0.6 (silica gel; ethyl acetate/petroleum ether=10:2, v/v).

ag) 1-(4-fluorobenzoyl)-4-[4-(2-oxazolin-2-yl)benzyl]piperidine from 4-[4-(2-oxazolin-2-yl)benzyl]piperidine and 4-fluorobenzoyl chloride. Melting point: 111°–113° C.

ah) 1-(4-tert.butylbenzoyl)-4-[4-(2-oxazolin-2-yl)benzyl] piperidine from 4-[4-(2-oxazolin-2-yl)benzyl]piperidine and 4-tert.butylbenzoyl chloride. Resin. $R_f$ value: 0.3 (Silica gel; ethyl acetate).

ai) 1-(4-biphenylcarbonyl)-4-[4-(2-oxazolin-2-yl)benzyl] piperidine from 4-[4-(2-oxazolin-2-yl)benzyl]piperidine and 4-biphenylcarbonyl chloride. Melting point: 158°–160° C.

aj) 1-(2-naphthylcarbonyl)-4-[4-(2-oxazolin-2-yl)benzyl] piperidine from 4-[4-(2-oxazolin-2-yl)benzyl]piperidine and 2-naphthalenecarbonyl chloride. Melting point: 100°–105° C.

ak) 1-(1-naphthylcarbonyl)-4-[4-(2-oxazolin-2-yl)benzyl] piperidine from 4-[4-(2-oxazolin-2-yl)benzyl]piperidine and 1-naphthalenecarbonyl chloride. Melting point: 70°–73° C.

al) 1-(4-chlorophenylsulphonyl)-4-[4-(2-oxazolin-2-yl)benzyl] piperidine from 4-[4-(2-oxazolin-2-yl) benzyl]piperidine and 4-chlorophenylsulphonyl chloride. Melting point: 155°–157° C.

am) 1-(4-methylbenzoyl)-4-[4-(2-oxazolin-2-yl)benzyl]piperidine from 4-[4-(2-oxazolin-2-yl) benzyl]piperidine and 4-methylbenzoyl chloride. Melting point: 143°–145° C.

an) 4-(4-cyanobenzoyl)-4-[4-(2-oxazolin-2-yl)benzyl]piperidine from 4-[4-(2-oxazolin-2-yl)benzyl]piperidine and 4-cyanobenzoyl chloride. Melting point: 148°–150° C.

ao) 4-[4-(2-oxazolin-2-yl)benzyl]-1-(4-pyridoyl)piperidine from 4-[4-(2-oxazolin-2-yl)benzyl]piperidine and isonicotinoyl chloride. Melting point: 148°–150° C.

ap) 1-(4-chlorobenzoyl)-3-[4-(2-oxazolin-2-yl)benzylidene] pyrrolidine from 3-[4-(2-oxazolin-2-yl)benzylidene]pyrrolidine and 4-chlorobenzoyl chloride. $R_f$ value: 0.36 (silica gel; methylene chloride/methanol= 24:1, v/v).

EXAMPLE 4

4-[4-(2-Oxazolin-2-yl) benzylidene]-1-(4-pentynoyl)piperidine 356 mg (2.2 mmol) of N,N'-carbonyldiimidazole in 3 ml of tetrahydrofuran are added to 200 mg (2 mmol) of 4-pentynoic acid in 2 ml of tetrahydrofuran at ambient temperature. The mixture is stirred at 40° C. for 1 hour. 363 mg (1.5 mmol) of 4-[4-(2-oxazolin-2-yl)benzylidene]piperidine are then added and the mixture is stirred at 40° C. for a further 2 hours. The reaction solution is then evaporated down and the residue is purified by column chromatography (Silica gel; ethyl acetate). 320 mg (66% of theory) of the title compound of melting point 118° C. are obtained.

$^1$H-NMR spectrum (200 MHz, $CDCl_3$); signals at ppm: 2.0 (s,1H), 2.3–2.7 (m,8H), 3.4–3.8 (m,4H), 4.05 (t,2H), 4.4 (t,2H), 6.4 (s,1H), 7.2 (d,2H), 2.9 (d,2H).

The following was obtained analogously:

a) 4-[4-(2-oxazolin-2-yl)benzylidene]-1-(4-phenyl-3-butenoyl)piperidine from 4-[4-(2-oxazolin-2-yl)benzylidene]piperidine, 4-phenyl- 3-butenoic acid and N,N'-carbonyldiimidazole. Melting point: 139° C.

EXAMPLE 5

4-[4-(2-Oxazolin-2-yl)benzyl]-1-(4-trifluoromethylbenzoyl)piperidine 441 mg (1 mmol) of 4-[4-(2-oxazolin-2-yl)benzylidene]-1-( 4-trifluoromethylbenzoyl)piperidine are hydrogenated (ambient temperature, 30 minutes, hydrogen pressure 50 psi) in 10 ml of anhydrous ethanol and 2.5 ml of ethyl acetate in the presence of 0.5 g of palladium-carbon (10%). The catalyst is then suction-filtered, the filtrate is evaporated under reduced pressure at a bath temperature of 50° C. and the residue is purified by column chromatography (Silica gel; ethyl acetate). 200 mg (48% of theory) of the title compound of melting point 115° C. are obtained.

$^1$H-NMR spectrum (200 MHz, $CDCl_3$); signals at ppm: 1.0–1.4 (m,2H), 1.6–1.9 (m,3H), 2.6 (d,2H), 2.7–3.1 (m,2H), 3.6 (m,1H), 4.05 (t,2H), 4.4 (t,2H), 4.7 (m, 1H), 7.15 (d,2H), 7.5 (d,2H), 7.65 (d,2H), 7.85 (d,2H).

The following were obtained analogously:

a) 1-(4-chlorobenzoyl)-4-[4-(R-4-methyl-2-oxazolin-2-yl)benzyl] piperidine from 1-(4-chlorobenzoyl)-4-[4-(R-4-methyl-2-oxazolin-2-yl)benzylidene] piperidine. Colourless resin. $R_f$ value: 0.37 (silica gel; ethyl acetate).
b) 1-(4-chlorobenzoyl)-4-[4-(2-oxazolin-2-yl)benzyl]piperidine from 1-(4-chlorobenzoyl)-4-[4-(2-oxazolin-2-yl)benzylidene] piperidine. Melting point: 136°–138° C.
c) 1-(4-chlorobenzoyl)-3-[4-(2-oxazolin-2-yl)benzyl]piperidine from 1-(4-chlorobenzoyl)-3-[4-(2-oxazolin-2-yl)benzylidene] piperidine. Colourless resin. $R_f$ value: 0.5 (silica gel; ethyl acetate).

EXAMPLE 6

1-(4-Chlorobenzoyl)-4-[2-fluoro-4-(2-oxazolin-2-yl)benzylidene] piperidine 0.4 g (0.95 mmol) of 1-(4-chlorobenzoyl)-4-[2-fluoro-4-(2-hydroxyethylaminocarbonyl)benzylidene]piperidine in 20 ml of tetrahydrofuran are treated with 0.3 g (1.1 mmol) of methyl N-(triethylamoniosulphonyl)carbamate (Burgess reagent) in portions, at boiling temperature, during the course of 45 minutes. The mixture is heated for a further 2 hours and evaporated down, and the residue is mixed with water, the mixture is extracted three times with methylene chloride, the extract is dried with anhydrous sodium sulphate and evaporated down, and the residue is purified on a Silica gel column (ethyl acetate/petroleum ether=10:4, v/v). 0.105 g (26% of theory) of the title compound of melting point 158°–160° C. is obtained.

$^1$H-NMR spectrum (200 MHz, DMSO-$d_6$); signals at ppm: 2.4 (m,4H), 3.4–3.7 (m,4H), 3.95 (t,2H), 4.4 (t,2H), 6.35 (s,1H), 7.3–7.7 (m,7H).

The following were prepared analogously:
a) 1-(4-chlorobenzoyl)-4-[3-methyl-4-(2-oxazolin-2-yl)benzylidene] piperidine from 1-(4-chlorobenzoyl)-4-[4-(2-hydroxyethylaminocarbonyl)-3-methylbenzylidene]piperidine and Burgess reagent. Melting point: 88°–90° C.
b) 4-[2-bromo-4-(2-oxazolin-2-yl)benzylidene]-1-(4-chlorobenzoyl)piperidine from 4-[2-bromo-4-(2-hydroxyethylaminocarbonyl)benzylidene]-1-(4-chlorobenzoyl)piperidine and Burgess reagent. Melting point: 185°–187° C.
c) 1-(4-chlorobenzoyl)-4-[2-methoxy-4-(2-oxazolin-2-yl)benzylidene] piperidine from 1-(4-chlorobenzoyl)-4-[4-(2-hydroxyethylaminocarbonyl)-2-methoxybenzylidene] piperidine and Burgess reagent. Melting point: 150°–152° C.

In the following, the preparation of pharmaceutical administration forms is described by some examples:

EXAMPLE I

Tablets containing 5 mg of
1-(4-chlorobenzoyl)-4-[4-(2-oxazolin-2-yl)benzylidene]piperidine

| Composition: | |
|---|---|
| 1 Tablet contains: | |
| Active compound | 5.0 mg |
| Lactose | 148.0 mg |
| Potato starch | 65.0 mg |
| Magnesium stearate | 2.0 mg |
| | 220.0 mg |

Preparation process:

A 10% strength mucilage is prepared from potato starch by heating. The active substance, lactose and the residual potato starch are mixed and granulated with the above mucilage through a sieve of mesh width 1.5 mm. The granules are dried at 45° C., again rubbed through the above mentioned sieve, mixed with magnesium stearate and pressed into tablets.

Tablet weight: 220 mg
Die: 9 mm

EXAMPLE II

Coated tablets containing 5 mg of
1-(4-chlorobenzoyl)-4-[4-(2-oxazolin-2-yl)benzylidene]piperidine The tablets prepared according to Example I are coated with a covering which essentially consists of sugar and talc according to a known process. The finished coated tablets are polished with the aid of beeswax. Coated tablet weight: 300 mg

EXAMPLE III

Suppositories containing 5 mg of
1-(4-chlorobenzoyl)-4-[4-(2-oxazolin-2-yl)benzylidene]piperidine

| Composition: | |
|---|---|
| 1 Suppository contains: | |
| Active compound | 5.0 mg |
| Suppository material (e.g. Witepsol W 45 ®) | 1695.0 mg |
| | 1700.0 mg |

Preparation process:

The finely powdered active substance is suspended in the molten suppository material, which has been cooled to 40° C. The material is poured out at 37° C. into slightly precooled suppository moulds. Suppository weight: 1.7 g.

EXAMPLE IV

Capsules containing 5 mg of
N-(4-chlorobenzoyl)-4-[4-(2-oxazolin-2-yl)benzylidene]piperidine

| Composition: | |
|---|---|
| 1 Capsule contains: | |
| Active substance | 5.0 mg |
| Lactose | 82.0 mg |
| Starch | 82.0 mg |
| Magnesium stearate | 1.0 mg |
| | 170.0 mg |

Preparation process:

The powder mixture is thoroughly mixed and filled into hard gelatine capsules of size 3 on a capsule filling machine, the final weight being continuously checked.

EXAMPLE V

Tablets containing 5 mg of 1-(4-chlorobenzoyl)-4-[4-(2-oxazolin-2-yl)benzyl]piperidine

| Composition: | |
|---|---|
| 1 Tablet contains: | |
| Active compound | 5.0 mg |
| Lactose | 148.0 mg |
| Potato starch | 65.0 mg |
| Magnesium stearate | 2.0 mg |
| | 220.0 mg |

Preparation process:

A 10% strength mucilage is prepared from potato starch by heating. The active substance, lactose and the residual potato starch are mixed and granulated with the above mucilage through a sieve of mesh width 1.5 mm. The granules are dried at 45° C., again rubbed through the above sieve, mixed with magnesium stearate and pressed into tablets.

Tablet weight: 220 mg
Die: 9 mm

EXAMPLE VI

Cream for topical application containing 1 g of 1-(4-chlorobenzoyl)-4-[4-(2-oxazolin-2-yl)benzylidene] piperidine A formulation for topical application of the compounds of the formula I may have the following composition

| | | |
|---|---|---|
| 1. | Active compound | 1.0 g |
| 2. | Stearyl alcohol | 4.0 g |
| 3. | Cetyl alcohol | 4.0 g |
| 4. | Mineral oil | 3.0 g |
| 5. | Polysorbate 60 | 4.5 g |
| 6. | Sorbitan stearate | 4.5 g |
| 7. | Propylene glycol | 10.0 g |
| 8. | Methylparaben | 0.18 g |
| 9. | Propylparaben | 0.02 g |
| 10. | Water | q.s. to 100.00 g |

Constituents 2–6 are heated to 80° C. until everything has melted. Constituent 1 is then dissolved in the oily phase. Constituents 7 and 10 are heated to 90° C. and constituents 8 and 9 are dissolved in the aqueous phase thus obtained. The aqueous phase is then added to the oil phase and stirred rapidly so that an emulsion is obtained. The mixture is then allowed to cool slowly to 50° C. in order to solidify the emulsion. The preparation is cooled to ambient temperature with further stirring.

The following example describes the preparation of a foodstuff for laying hens:

EXAMPLE VII

Foodstuff for laying hens, containing as active compound 1-(4-chlorobenzoyl)-4-[4-(2-oxazolin-2-yl)benzylidene]piperidine

| Maize | 633 g/kg |
|---|---|
| Soya bean flour | 260 g/kg |
| Meat meal | 40 g/kg |
| Feed fat | 25 g/kg |
| Soya oil | 17 g/kg |
| Bicalcium phosphate | 12 g/kg |
| Calcium carbonate | 6 g/kg |
| Vitamin/mineral mixture | 5 g/kg |
| Active compound | 2 g/kg |

After careful mixing of these components in the amounts indicated 1 kg of feed is obtained.

What we claim is:

1. An arylidene-1-azacycloalkane or arylalkyl-1-azacycloalkane of the formula I $$\text{(I)}$$

wherein:

n denotes the numbers 0 or 1;

m denotes the numbers 1 or 2;

p denotes the numbers 0 or 1;

A denotes a single bond, a straight-chained or branched $C_{1-17}$-alkylene group, a $C_{2-17}$-alkenylene group or a $C_{2-4}$-alkynylene group;

$W^1$ and $W^2$ each denote a hydrogen atom or together denote a carbon-carbon bond;

X denotes a carbonyl or sulphonyl group;

Y denotes an oxygen or sulphur atom or an $>NR^{11}$ group;

$R^1$ to $R^6$ in each case denote a hydrogen atom, or one, two or three of the groups $R^1$ to $R^6$, which groups may be identical or different, denote a straight-chained or branched $C_{1-4}$-alkyl group which may be substituted by a hydroxy, alkoxy, alkylthio or dialkylamino group or by a phenyl group which is optionally substituted by a halogen atom or an alkyl group, or denote an alkoxycarbonyl group and the remaining groups $R^1$ to $R^6$ each denote a hydrogen atom;

whilst one, two or all three of the groups $R^1$, $R^3$ and $R^5$ may also denote a phenyl group which is optionally substituted by an alkyl group or by a halogen atom;

$R^7$ denotes a hydrogen or halogen atom, or an alkyl or alkoxy group;

$R^8$ and $R^9$ independently of one another each denote a hydrogen atom or an alkyl group;

$R^{10}$ denotes a hydrogen atom, a $C_{3-6}$-cycloalkyl group, a phenyl group optionally substituted by a halogen atom, by a straight-chained or branched $C_{1-4}$-alkyl group, or by a trifluoromethyl, alkoxy, cyano, nitro, alkylsulphonyl or phenyl group, or $R^{10}$ denotes a phenyl group substituted by two trifluoromethyl groups, by two to five halogen atoms or by a halogen atom and an alkyl group, or $R^{10}$ denotes a naphthyl or tetrahydronaphthyl group optionally substituted by a fluorine atom, or $R^{10}$ denotes a pyridyl group or a thienyl group optionally substituted by a halogen atom or by an alkyl group; and $R^{11}$ denotes a hydrogen atom or an alkyl group;

whilst A cannot be a single bond if X denotes the sulphonyl group and $R^{10}$ denotes a hydrogen atom, and wherein, unless otherwise stated, the above mentioned alkyl, alkoxy, alkylthio and alkylsulphonyl groups each contain 1, 2 or 3 carbon atoms and the above mentioned halogen atoms are selected from fluorine, chlorine and bromine, or a pharmaceutically acceptable salt thereof.

2. An arylidene-1-azacycloalkane or arylalkyl-1-azacycloalkane of the formula Ia

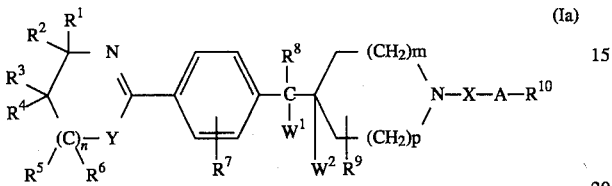

wherein:

n denotes the numbers 0 or 1;

m denotes the numbers 1 or 2;

p denotes the number 0 or 1;

A denotes a single bond, a straight-chained or branched $C_{1-17}$-alkylene group, or a $C_{2-4}$-alkenylene or a $C_{2-4}$-alkynylene group;

$W^1$ and $W^2$ each denote a hydrogen atom or together denote a carbon-carbon bond;

X denotes a carbonyl or sulphonyl group;

Y denotes an oxygen or sulphur atom or an $>NR^{11}$ group;

$R^1$ to $R^4$ in each case denote a hydrogen atom, or one or two of the groups $R^1$ to $R^4$ independently of one another each denote a straight-chained or branched $C_{1-4}$-alkyl group which may be substituted by a hydroxy, alkylthio or dialkylamino group or by a phenyl group itself optionally substituted by a halogen atom, or denote a phenyl group, and the remaining groups $R^1$ to $R^4$ each denote a hydrogen atom;

$R^5$ and $R^6$, which may be identical or different, denote a hydrogen atom or a methyl group;

$R^7$ denotes a hydrogen or halogen atom, or an alkyl or alkoxy group;

$R^8$ denotes a hydrogen atom or an alkyl group;

$R^9$ denotes a hydrogen atom;

$R^{10}$ denotes a hydrogen atom, a $C_{3-6}$-cycloalkyl group, a phenyl group optionally substituted by one or two halogen atoms, by a straight-chained or branched $C_{1-4}$-alkyl group or by a trifluoromethyl, methoxy, cyano, nitro, methylsulphonyl or phenyl group, or $R^{10}$ denotes a phenyl group substituted by two trifluoromethyl groups or by a halogen atom and a methyl group, or $R^{10}$ denotes a phenyl group substituted by three to five fluorine atoms, or $R^{10}$ denotes a naphthyl group optionally substituted by a fluorine atom, or $R^{10}$ denotes a tetrahydronaphthyl or pyridyl group or a thienyl group optionally substituted by a halogen atom; and $R^{11}$ denotes a hydrogen atom or an alkyl group;

whilst A cannot be a single bond if X denotes the sulphonyl group and $R^{10}$ denotes a hydrogen atom, and wherein, unless otherwise stated, the above mentioned alkyl groups each contain 1, 2 or 3 carbon atoms and the above mentioned halogen atoms are selected from the group consisting of fluorine, chlorine and bromine, or a pharmaceutically acceptable salt thereof.

3. An arylidene-1-azacycloalkane or arylalkyl-1-azacycloalkane of the formula Ia, in accordance with claim 2, wherein:

n denotes the numbers 0 or 1, m denotes the numbers 1 or 2, p denotes the numbers 0 or 1, A denotes a single bond, a $C_{1-17}$-straight-chained or branched alkylene or $C_{2-4}$-alkenylene group, $W^1$ and $W^2$ each denote a hydrogen atom or together denote a carbon-carbon bond, X denotes a carbonyl or sulphonyl group, Y denotes an oxygen atom or an $>NR^{11}$ group, $R^1$ to $R^4$ in each case denote a hydrogen atom or one or two of the groups $R^1$ to $R^4$ independently of one another in each case denote a straight-chained or branched $C_{1-4}$-alkyl group, and the remaining groups $R^1$ to $R^4$ each denote a hydrogen atom, $R^5$ and $R^6$, which may be identical or different, denote a hydrogen atom or a methyl group, $R^7$ denotes a hydrogen or halogen atom, or a methyl or methoxy group, $R^8$ denotes a hydrogen atom or a methyl group, $R^9$ denotes a hydrogen atom, $R^{10}$ denotes a hydrogen atom, a $C_{3-6}$-cycloalkyl group, a phenyl group optionally substituted by one or two halogen atoms, by five fluorine atoms, by an alkyl group, by one or two trifluoromethyl groups or by a halogen atom and an alkyl group, or $R^{10}$ denotes a 1-naphthyl group which is optionally substituted in the 4-position by a fluorine atom, or $R^{10}$ denotes a 2-naphthyl group, a 1,2,3,4-tetrahydro-2-naphthyl group, a pyridyl or 4-biphenyl group or a thienyl group optionally substituted by a halogen atom, and $R^{11}$ denotes a hydrogen atom or a methyl group, whilst A cannot be a single bond if X denotes the sulphonyl group and $R^{10}$ denotes a hydrogen atom, and wherein, unless otherwise stated, the above mentioned alkyl moieties each contain 1, 2 or 3 carbon atoms and the above mentioned halogen atoms are selected from the group consisting of fluorine and chlorine, or a pharmaceutically acceptable salt thereof.

4. An arylidene-1-azacycloalkane or arylalkyl-1-azacycloalkane of the formula Ia, in accordance with claim 2, wherein:

n denotes the numbers 0 or 1, m denotes the number 1, p denotes the numbers 0 or 1, A denotes a single bond, $W^1$ and $W^2$ each denote a hydrogen atom or together denote a carbon-carbon bond, X denotes a carbonyl group, Y denotes an oxygen atom, $R^1$ to $R^6$ in each case denote a hydrogen atom, $R^7$ denotes a hydrogen or halogen atom or a methyl group, $R^8$ and $R^9$ each denote a hydrogen atom, $R^{10}$ denotes a phenyl group substituted in the 4-position by a fluorine, chlorine or bromine atom or by a trifluoromethyl group, or $R^{10}$ denotes a 4-chloro-3-methylphenyl group, a 5-chloro-2-thienyl group or a cyclohexyl group, or a pharmaceutically acceptable salt thereof.

5. A compound selected from the group consisting of:
(1) 1-(4-chlorobenzoyl)-4-[4-(2-oxazolin-2-yl)benzylidene] piperidine
(2) 1-(4-chlorobenzoyl)-4-[4-(4,5-dihydro-6H-oxazin-2-yl)benzylidene] piperidine
(3) 4-[4-(2-oxazolin-2-yl)benzylidene]-1-(4-trifluoromethylbenzoyl)piperidine
(4) 1-(4-chloro-3-methylbenzoyl)-4-[4-(2-oxazolin-2-yl)benzylidene] piperidine
(5) 1-(4-fluorobenzoyl)-4-[4-(2-oxazolin-2-yl)benzylidene] piperidine
(6) 1-(5-chloro-2-thienoyl)-4-[4-(2-oxazolin-2-yl)benzylidene] piperidine
(7) 1-cyclohexanecarbonyl-4-[4-(2-oxazolin-2-yl)benzylidene] piperidine
(8) 4-[4-(2-oxazolin-2-yl)benzyl ]-1-(4-trifluoromethylbenzoyl)piperidine
(9) 1-(4-chlorobenzoyl)-4-[4-(2-oxazolin-2-yl)benzyl]piperidine
(10) 1-(4-chlorobenzoyl)-3-[4-(2-oxazolin-2-yl)benzylidene] pyrrolidine
(11) 1-(4-chlorobenzoyl)-4-[2-fluoro-4-(2-oxazolin-2-yl)benzylidene] piperidine (12) 1-(4-chlorobenzoyl)-4-[3-methyl-4-(2-oxazolin-2-yl)benzylidene] piperidine
and the pharmaceutically acceptable salts thereof.

6. A pharmaceutical composition, suitable for the treatment of hyperlipidaemias, hypercholesterolaemias and of atherosclerosis, comprising a compound according to claim 1, 2, 3, 4 or 5 together with a pharmaceutically acceptable carrier.

7. A method for the treatment of excessive cholesterol biosynthesis, which method comprises administering to a host in need of such treatment an effective amount of a compound according to claim 1, 2, 3, 4 or 5.

8. The method of claim 7 wherein the condition to be treated is hyperlipidaemia, hypercholesterolaemia or atherosclerosis.

9. The method of claim 8 wherein the condition to be treated or prevented is hyperlipidemia.

10. A method for the treatment of conditions caused by excessive cell proliferation, which method comprises administering to a host in need of such treatment an effective amount of a compound according to claim 1.

11. A method for the treatment of gallstones, which method comprises administering to a host in need of such treatment an effective amount of a compound according to claim 1, 2, 3, 4 or 5.

12. A method for the treatment of mycoses, which method comprises administering to a host in need of such treatment an effective amount of a compound according to claim 1, 2, 3, 4 or 5.

13. The method of claim 10, which method comprises administering an effective amount of the compound 1-(4-chlorobenzoyl)-4-[4-(2-oxazolin-2-yl)benzylidene] piperidine.

14. A method for the treatment of conditions caused by excessive cell proliferation, which method comprises administering to a host in need of such treatment an effective amount of a compound according to claim 2.

15. A method for the treatment of conditions caused by excessive cell proliferation, which method comprises administering to a host in need of such treatment an effective amount of a compound according to claim 3.

16. A method for the treatment of conditions caused by excessive cell proliferation, which method comprises administering to a host in need of such treatment an effective amount of a compound according to claim 4.

17. A method for the treatment of conditions caused by excessive cell proliferation, which method comprises administering to a host in need of such treatment an effective amount of a compound according to claim 5.

* * * * *